(12) United States Patent
Chaudhuri

(10) Patent No.: US 8,617,528 B2
(45) Date of Patent: Dec. 31, 2013

(54) COMPOSITIONS AND METHODS FOR STABILIZING INGREDIENTS USING 2,4-PENTANEDIONE COMPOUNDS

(75) Inventor: Ratan K. Chaudhuri, Lincoln Park, NJ (US)

(73) Assignee: Sytheon Ltd., Boonton, NJ (US)

( * ) Notice: Subject to any disclaimer, the term of this patent is extended or adjusted under 35 U.S.C. 154(b) by 0 days.

(21) Appl. No.: 13/310,924

(22) Filed: Dec. 5, 2011

(65) Prior Publication Data

US 2012/0141395 A1 Jun. 7, 2012

Related U.S. Application Data

(60) Provisional application No. 61/419,961, filed on Dec. 6, 2010.

(51) Int. Cl.
*A61K 8/35* (2006.01)
*C07C 45/86* (2006.01)
*C07C 49/14* (2006.01)

(52) U.S. Cl.
USPC .......................... 424/70.9; 568/303; 562/459

(58) Field of Classification Search
None
See application file for complete search history.

(56) References Cited

U.S. PATENT DOCUMENTS

| | | | |
|---|---|---|---|
| 3,278,448 A * | 10/1966 | Lauerer et al. | 252/589 |
| 3,856,911 A | 12/1974 | Yokotani et al. | |
| 4,281,080 A | 7/1981 | Bullard et al. | |
| 5,288,750 A | 2/1994 | Pohto et al. | |
| 6,602,515 B2 | 8/2003 | Chaudhuri | |
| 6,831,191 B2 | 12/2004 | Chaudhuri | |
| 7,150,876 B2 | 12/2006 | Chaudhuri et al. | |
| 7,445,729 B2 | 11/2008 | Faryniarz et al. | |
| 2005/0244349 A1* | 11/2005 | Chaudhuri et al. | 424/59 |
| 2006/0216251 A1 | 9/2006 | Morariu | |
| 2007/0059258 A1 | 3/2007 | Chaudhuri | |
| 2009/0202464 A1 | 8/2009 | Flachsmann | |
| 2009/0304620 A1 | 12/2009 | Schulze Zur Wiesche et al. | |

FOREIGN PATENT DOCUMENTS

| | | |
|---|---|---|
| AU | 2005284472 B2 | 3/2006 |
| CA | 2128926 A1 | 1/1995 |
| EP | 0440324 A2 | 8/1991 |
| EP | 0636647 A1 | 2/1995 |
| GB | 949181 A | 2/1964 |
| JP | 2001328357 A1 | 11/2001 |
| WO | 2006029686 A1 | 3/2006 |
| WO | 2006076821 A1 | 7/2006 |
| WO | 2007143873 A1 | 12/2007 |

OTHER PUBLICATIONS

Sidhu, Anjali et. al., "Condensation of Acetylacetone with Imineones: A Chemoselective Reation", J. Ind. Council Chem 2009, vol. 26, 136-138.
Memarian, Hamid R. et al., "Synthesis of Some New Unsymmetrically Substituted 1,4-Dihydropyridines", Zeitschrift fuer Naturforschung 2006.
Pathak, Vijai N. et. al., "Synthesis, Spectral Studies and Antimicrobial Activity of 7-Chlor-2-alkyl/aryl-4-alkyl/aryl-3-arylidene-3H-1,5-benzodiazepines", Indian J. of Chem. 2007, vol. 46B, 1191-1197.

\* cited by examiner

*Primary Examiner* — Frederick Krass
*Assistant Examiner* — Michael P Cohen
(74) *Attorney, Agent, or Firm* — Edward K Welch, II; IP&L Solutions

(57) ABSTRACT

Benzylidene substituted 2,4-pentanedione compounds without having phenolic hydroxyl group(s) are found to provide photostability to otherwise photosensitive compounds and compositions.

14 Claims, No Drawings

US 8,617,528 B2

COMPOSITIONS AND METHODS FOR STABILIZING INGREDIENTS USING 2,4-PENTANEDIONE COMPOUNDS

This application claims the benefit of U.S. Provisional Patent Application No. 61/419,961, filed on Dec. 6, 2010, which is hereby incorporated herein by reference in its entirety.

FIELD OF THE INVENTION

The present invention relates to benzylidene substituted 2,4-pentanedione compounds without having phenolic hydroxyl group(s) and the use thereof as stabilizer additives for use in various food, cosmetic, health and beauty aid, otherwise known as personal care, products and household products as well as in various photosensitive components or ingredients incorporated into those products such as sunscreens actives, flavors, fragrances, colors, antioxidants, vitamins and the like. These compounds protect against the degradation of such products and components resulting from exposure to sun light, heat and/or air thereby maintaining, or minimizing any loss in, efficacy, storage stability, viscosity, and/or color of the formulated products. The present inventive compounds have chelating ability whereby transition metal induced oxidative instability of photosensitive compounds and associated skin damage can be mitigated. Additionally, these compounds have broad pH stability.

BACKGROUND OF THE INVENTION

Many additives for food, cosmetic, personal care and household products and the products into which they are incorporated are light sensitive owing to the ability of such additives to absorb radiation from UV and/or visible light. Such products and additives include sunscreens, organic colorants, dyes, antioxidants, fragrances, flavor ingredients, etc. These compounds can be elevated to a higher energy level (excited state) upon absorption of radiation. As such, they are more reactive than in their normal or ground state and will readily react with other molecules or breakdown into lower energy degradation products. The consequence of these reactions is a significant, if not complete, loss of product integrity, color loss, malodor, viscosity changes etc. of the products into which they are formulated. The probability of reaction or decomposition is directly related to the length of time the molecules remain in the excited state.

One method of addressing light sensitivity is through the use of light, especially UV light, absorbing chromophores; however, these do not block all light nor potential degradation pathways for photosensitive compounds. Another approach is through the quenching of excited chromophores. Quenching of excited chromophores reduces the lifetime of excited states thereby reducing the side reactions of excited state intermediates. Both methods result in some improvement in shelf life/shelf stability for formulated products. It would be desirable and beneficial to be able to combine UV-light absorbing capability with the ability to quench the excited state within a single molecule.

Achieving photostable sun and skin care formulations is a huge challenge to the formulator because of inherent instabilities of certain organic compounds, especially certain sunscreens like [1-3] (4-tert-butyl-4'-methoxy-dibenzoylmethane, Avobenzone, a UV-A sunscreen; antioxidants like natural Tocopherols and Carotenoids; fragrances such as Vanillin; colorants such as Guaiazulene; retinoids; water-soluble dyes; etc. Currently available photostabilizers satisfy the need to stabilize photosensitive compounds mostly in the acidic pH range but are unable to effectively reduce photofragmentation under UV-exposure when the formulation pH is basic or near neutral.

Topical sunscreen compositions are commonly used during outdoor work or leisure as a means for providing protection of exposed skin against acute and chronic adverse effects of solar radiation such as sunburn, cancer and photo-aging. Many effective sunscreen preparations are sold commercially and/or are described in the cosmetic and pharmaceutical literature. In general sunscreen preparations are formulated as creams, lotions, spray or oils containing, as the active agent, an ultra violet radiation absorbing or blocking compound. The sunscreen functions by absorbing or blocking ultra-violet radiation preventing its penetration into the skin. Although sunscreens do prevent erythema and are recommended to be used as part of safe-sun practices, current research suggests that photoprotection is also needed to reduce skin damage (K M Hanson and R T Clegg, Bioconvertible vitamin antioxidants improve sunscreen photoprotection against UV-induced reactive oxygen species, J Cosmet Sci, 54:589-598, 2003).

Organic sunscreens are classified into UV-A filters, UV-B filters or broad spectrum filters (UV-A and UV-B functionality in a single molecule) depending on the type of radiation they absorb. UV-A sunscreens absorb radiation in the 320 to 400 nm regions of the ultra violet spectrum and UV-B sunscreens absorb radiation in the 290 to 320 nm regions of the ultra violet spectrum (See Sunscreens, Regulations and Commercial Development, Third Edition, Nadim A. Shaath, Ed., Taylor & Francis, 2005). Broad-spectrum sunscreens (UV-A and UV-B functionality) absorb radiation in the 290 to 400 nm region of the ultra violet spectrum and have two maximums, one in the UV-B region and the other in the UV-A region. Representative references relating to UV sunscreens include Gonzalez et. al.—U.S. Pat. No. 7,186,404; Aust et. al.—U.S. Pat. No. 7,175,834; Roseaver et. al.—U.S. Pat. No. 7,172,754; Simoulidis et. al.—U.S. Pat. No. 7,175,835; Mongiat et. al.—U.S. Pat. No. 7,101,536; Maniscalco—U.S. Pat. No. 7,078,022; Chaudhuri et. al.—U.S. Pat. No. 6,165,450; Forestier et. al. U.S. Pat. No. 5,175,340; and Wang et. al. U.S. Pat. No. 5,830,441.

Unfortunately, some of the highly chromophoric monomeric organic compounds employed in sunscreen compositions are not photostable and the protection they may otherwise provide against sun damage is lost after only a short period of time. For example, Avobenzone, a UV-A sunscreen, is generally photo-unstable and, while certain combinations of sunscreens are found to provide broader sun protection, the photo-instability of Avobenzone increases significantly when combined with other sunscreen actives such as octyl methoxycinnamate (a UV-B organic sunscreen) thereby resulting in an even shorter period of protection. This is surprising since octyl methoxycinnamate (OMC) has been regarded as relatively photostable in accordance with most studies; however, the absorption maxima of Avobenzone (about 360 nm) and OMC (about 310 nm) do not overlap sufficiently to allow directly excited singlet-singlet energy transfer to occur. Such an energy transfer from one excited triplet-state to another is possible provided the absorption energy levels of each component sufficiently overlap to allow for the transfer and, hence, an additive effectiveness.

Octocrylene, a UV-B absorber, has found widespread use in sunscreen formulations because of its photostability and perceived non-irritant and non-sensitizer properties, Octocrylene has been found to be an excellent photostabilizer for Avobenzone; however, recent studies have reported many instances of contact allergy (CA) and photocontact allergy (PCA) to octocrylene (A Bennàssar, R Grimalt, C Romaguera, J Vilaplana, "Two cases of photocontact allergy to the new sun filter octocrylene", Dermatology Online Journal, 15(12):14, 2009; D Pascoe, L Moreau and D Sasseville, "Emergent and unusual allergens in cosmetics", Dermatitis, 21(3):127-137, 2010; D Delplace and A Blondeel A, "Octocrylene: really non-allergenic?", Contact Dermatitis, 54(5): 295, 2006).

A recent study based on in vitro approaches was performed to demonstrate that photostability is an essential requirement to protect against UVA-induced genetic and dermal alterations (L Marrot, J P Belaïdi, F Lejeune, J R Meunier, D Asselineau, F Bernard, "Photostability of sunscreen products influences the efficiency of protection with regard to UV-induced genotoxic or photoaging-related endpoints", British J Dermatol, 151(6):1234-1244, 2006). The protection afforded by two sunscreen products, differing with regard to their photostability, was studied by the authors using biological markers related to the genotoxic or photoaging impact of UVA or simulated solar UV radiation (UV-SSR). Comet assay was used to assess direct DNA breakage, photo-oxidized purines and lomefloxacin-induced DNA breaks in nuclei of normal human keratinocytes in culture. In similar conditions, detection of p53 accumulation was performed. Results showed that photo-unstable sunscreen products causes: (a) formation of sunburn cells; (b) DNA damage with increased formation of pyrimidine dimers; (c) dermal alterations with superficial fibroblasts; higher dose causes destruction of dermal fibroblasts and (d) formation of higher level of MMP-1

Various techniques for stabilizing UV absorbent compositions are known. Representative disclosures in this area include Forestier et. al.—U.S. Pat. No. 5,567,418, U.S. Pat. No. 5,538,716, and U.S. Pat. No. 5,951,968; Deflandre et. al.—U.S. Pat. No. 5,670,140; Chaudhuri—U.S. Pat. No. 8,003,082, 7,150,876, 6,831,191, 6,602,515, 7,166,273, 6,936,735, 6,831,191, and 6,699,463; Chaudhuri et. al.—U.S. Pat. No. 7,150,876; and Bonds et. al. U.S. Pat. No. 6,962,692. In an effort to address some of the shortcomings of typical sunscreen compositions, certain manufacturers have added antioxidants. Antioxidants are believed to provide protection from free-radical damage by quenching or sequestering free radicals generated by UV exposure. Photo-protective products combining sunscreens and an antioxidant or antioxidant mixtures have been touted as providing increased efficacy and safety relative to UV exposure (S R Pinnell, "Cutaneous Photodamage, Oxidative Stress; and Topical Antioxidant Protection", J Am Acad Dermatol, 48: 1-19, 2003). To be an effective quencher, it is believed that the antioxidant must be present in an adequate concentration at the site of free radical generation. However, since antioxidants are used in relatively low concentrations and are a separate ingredient, they may not be available at the site of free radical generation. Consequently, the level of skin protection may be reduced and, oftentimes, less than desired.

While the general use of antioxidants in sunscreen formulations is advocated, the fact that many of these compounds not only function as antioxidants, but intrinsically have pro-oxidant action as well, especially in the presence of transition metals, is oftentimes overlooked or disregarded. (See e.g., "Role of Antioxidants in Sun Care Products" by R. Chaudhuri in Sunscreens, N A Shaath, editor, Taylor and Francis, p 603-638, 2005). Pro-oxidant action is seen with even well-known antioxidants such as vitamin C (ascorbate), vitamin E (tocopherols), glutathione and proanthocyanidins (from pine and grape). The pro-oxidant activity of vitamin C results from the reduction of $Fe^{3+}$ to $Fe^{2+}$ and its reaction with $H_2O_2$ to generate OH radicals. Pro-oxidant effects are not unique to vitamin C: they can be demonstrated with many reducing agents, including vitamin E, glutathione and several plant phenolic compounds, in the presence of transition metal ions. Thus, if vitamin C's pro-oxidant effects are relevant, the pro-oxidation effects of these other reductants may also be expected to occur.

Ideally, sun and skin care products should be such that no or minimal photochemical instability or photosensitizing transformations of its components occur within the formulation or on the skin. Photochemical stability is indeed the most important characteristic of an effective UV filter since the light-induced degradation of the sunscreen agent not only reduces its photoprotective efficacy, but can also promote phototoxic or photoallergic contact dermatitis (V A DeLeo, S M Suarez, M J Maso, "Photoallergic contact dermatitis", Arch. Dermatol. 128:113-118, 1992; R. Haywood, P Wardman, R Sanders & C Linge, "Sunscreens inadequately protect against ultraviolet-A-induced free radicals in skin: implications for skin aging and melanoma?", J. Invest. Dermatol, 121:862-868, 2003). This is not only true for sunscreens; but also true for other formulation ingredients. Photo-instability can result in the formation of singlet oxygen species, thereby causing damage to biomolecules such as DNA, proteins, lipids, etc. (J L Ravanat, G R Martinez, M H Medeiros, P Di Mascio and J Cadet, "Mechanistic aspects of the oxidation of DNA constituents mediated by singlet molecular oxygen", Arch. Biochem Biophys, 423:23-30, 2004; J L Ravanat, S Sauvaigo, S Caillat, G R Martinez, M H G Medeiros, P Di Mascio, A Favier and J Cadet, "Singlet oxygen-mediated damage to cellular DNA determined by the comet assay associated with DNA repair enzymes", Biol. Chem. 385: 17-20, 2004; M J Davies, "Reactive species formed on proteins exposed to singlet oxygen", Photochem. Photobiol. Sci. 3:17-25, 2004; I. Tejero I, A Gonzalez-Lafont, J M. Lluch and L A Eriksson, "Photo-oxidation of lipids by singlet oxygen: a theoretical study", Chem Phys Lett, 398:336-342, 2004; C Kielbassa and B. Epe, "DNA damage by UV and visible light and its wavelength dependence", Methods Enzymol, 319: 436-445, 2000)

Since Avobenzone is a very desirable UV-A sunscreen component of many sunscreen products and its photo-instability is known, considerable effort has been devoted to studies of these instabilities (C A Bonda, "The photostability of organic sunscreens: A review" In: Shaath N A, ed. Sunscreens, New York, Taylor & Francis, 2005; 321-349). Furthermore, it is believed that there are more than 170 issued US patents that are related in one way or another to the photo-stabilization of avobenzone (dibenzoylmethane). Representative patent publications include those set forth in Table 1.

TABLE 1

| | | |
|---|---|---|
| 1 | 8,003,082 | Photostable organic sunscreen composition |
| 2 | 7,544,350 | Method of decreasing the UV light degradation of polymers |
| 3 | 7,186,404 | Photostable sunscreen compositions and methods of stabilizing |
| 4 | 6,444,195 | Sunscreen compositions containing a dibenzoylmethane derivative |
| 5 | 6,426,428 | UV-photoprotective dibenzoylmethane compositions comprising photostabilizing amounts of benzalmalonate silanes |
| 6 | 6,312,673 | Photostabilized sunscreen compositions comprising dibenzoylmethane compounds and benzylidenecamphor-substituted silanes/organosiloxanes |
| 7 | 6,290,938 | Sunscreen compositions |
| 8 | 6,224,854 | UV protection compositions |

TABLE 1-continued

| | | |
|---|---|---|
| 9 | 6,174,517 | Compositions containing a dibenzoylmethane derivative and a titanium oxide nanopigment, and uses |
| 10 | 6,071,501 | Photostable UV protection compositions |
| 11 | 5,976,513 | UV protection compositions |
| 12 | 5,972,316 | UV protection compositions |
| 13 | 5,968,485 | UV protection compositions |
| 14 | 5,951,968 | UV-photoprotective dibenzoylmethane compositions comprising photostabilizing amounts of benzalmalonate silanes |
| 15 | 5,788,954 | Hydrating skin care and sunscreen composition containing dibenzoylmethane derivative, E.G., parsol 1789, and C12, C16, C18 branched chain hydroxybenzoate and/or C12, C16, branched chain benzoate stabilizers/solubilizers |
| 16 | 5,783,173 | Stable sunscreen composition containing dibenzoylmethane derivative, E.G., PARSOL 1789, and C12, C16, C18 branched chain hydroxybenzoate and/or C12, C16, branched chain benzoate stabilizers/solubilizers |
| 17 | 5,567,418 | Process for stabilizing 4-(1,1-dimethylethy)-4' methoxydibenzoyl-methane against UV radiation |
| 18 | 5,538,716 | Photostable cosmetic screening composition containing a UV-A screening agent and a (4-methoxybenzylidene)cyanoacetate |

Among the various compounds that have been tested and evaluated, certain benzylidene malonate esters having antioxidant functionality have been identified as good photo-stabilizers for stabilizing photo-unstable compounds like sunscreens, antioxidants, dyes, vitamins, flavors, fragrance and other food, cosmetic and health and beauty aid product ingredients. Representative disclosures in this area are set forth in the Table 2.

TABLE 2

| | | |
|---|---|---|
| 1 | 8,003,082 | Photostable organic sunscreen composition |
| 2 | 7,166,273 | Photo stable organic sunscreen compositions |
| 3 | 7,150,876 | Methods for stabilizing ingredients within cosmetics, personal care and household products |
| 4 | 6,936,735 | Photostable cationic organic sunscreen compounds and compositions obtained therefrom |
| 5 | 6,831,191 | Photo stable organic sunscreen compounds with antioxidant properties and compositions obtained therefrom |
| 6 | 6,699,463 | Photostable cationic organic sunscreen compounds with antioxidant properties and compositions obtained therefrom |
| 7 | 6,602,515 | Photo stable organic sunscreen compounds with antioxidant properties and compositions obtained therefrom |

Antioxidant, photo-stabilizer compounds described in the above referenced patent literature are commercially available under the trade names Oxynex® ST (Diethylhexyl syringylidene malonate) and Oxynex® ST Liquid (blend of Oxynex® ST and caprylic/capric triglycerides). These have been shown to stabilize Avobenzone and other photo-unstable compounds. Unfortunately, Oxynex® ST is not an effective broad spectrum antioxidant and its effectiveness drops significantly when exposed to UV irradiation above 40 Joules/cm$^2$.

Another class of ingredients of cosmetic and health and beauty aid products that manifest photo-instability is the retinoids. These compounds are an especially important class of drugs used to treat a variety of health conditions including acne, photoaging, psoriasis, ichthyosis, hair loss, and various cancers and generally consist of four isoprenoid units joined in a head to tail manner. All retinoids may be derived from a monocyclic parent compound containing five carbon-carbon double bonds and a functional group at the terminus of the acyclic portion. The retinoids include Vitamin A (retinol) and its natural and synthetic derivatives, analogues, and metabolites that exhibit biological activity qualitatively similar to retinol. Particularly important retinoids include retinol, retinyl esters, retinal, and isomers of retinoic acid, including all-trans-retinoic acid (tretinoin) and cis-isomeric retinoic acids, e.g., 13-cis-retinoic acid (isotretinoin) and 9-cis-retinoic acid. The naturally occurring retinoids are essential for many of life's processes including vision, reproduction, metabolism, differentiation, bone development, and pattern formation during embryogenesis.

Retinoids, however, are extremely sensitive to UV light, air, and oxidizing agents due to their high degree of unsaturation. For example, tretinoin must be stored under an atmosphere of inert gas (e.g., argon) in the dark at <−20° C. to preserve its integrity and biological activity. While solutions of tretinoin in pure organic solvents are stable when stored in the dark, aqueous solutions deteriorate quickly. Retinoids are lipophilic. For example, tretinoin is practically insoluble in water, slightly soluble in ethanol (3 mg/ml) and chloroform, sparingly soluble in ether, and soluble in methylene chloride and dimethyl sulfoxide (40 mg/ml).

Banda (U.S. Pat. No. 6,551,605) has shown that certain diesters of naphthalene dicarboxylic acid are good solvents for retinoids. For example, isotretinoin is soluble in the diethylhexyl diester of 2,6-naphthalene-dicarboxylic acid at approximately 6.7 mg/ml, and tretinoin is soluble in the same diester at approximately 5.6 mg/ml. While solutions of tretinoin in pure organic solvents are stable when stored in the dark, aqueous solutions deteriorate quickly. A solution of a retinoid such as tretinoin or isotretinoin in a diester of naphthalene dicarboxylic acid has been shown to be quite stable if kept in the dark.

Di- or poly-esters of naphthalene have been claimed to be effective solubilizers and stabilizers for a wide variety of photosensitive compounds. Representative disclosures in this regard as set forth in the Table 3.

TABLE 3

| | | |
|---|---|---|
| 1 | 7,799,317 | Photostabilizers, UV absorbers, and methods of photostabilizing compositions |
| 2 | 6,518,451 | Diesters of naphthalene dicarboxylic acid |
| 3 | 6,444,195 | Sunscreen compositions containing a dibenzoylmethane derivative |
| 4 | 6,284,916 | Diesters of naphthalene dicarboxylic acid |
| 5 | 6,180,091 | Compositions containing diesters or polyesters of naphthalene dicarboxylic acid and methods for imparting hair gloss and to provide hair color and hair dye stabilization |
| 6 | 6,129,909 | Compositions containing diesters or polyesters of naphthalene dicarboxylic acid and methods for imparting hair gloss and to provide hair color and hair dye stabilization |
| 7 | 6,126,925 | Photostable sunscreen compositions containing dibenzoylmethane derivative, e.g., PARSOL ® 1789, and diesters of naphthalene dicarboxylic acid photostabilizers and enhancers of the sun protection factor (SPF) |
| 8 | 6,113,931 | Clear formulations containing diesters or polyesters of naphthalene dicarboxylic acid |
| 9 | 5,993,789 | Photostable sunscreen compositions containing dibenzoylmethane derivative, E.G., parsol ® 1789, and diesters or polyesters of naphthalene dicarboxylic acid photostabilizers and enhancers of the sun protection factor (SPF) |
| 10 | 5,849,273 | Skin care and sunscreen composition containing dibenzoylmethane derivative, e.g., parsol ® 1789, and $C_{12}$, $C_{16}$, $C_{18}$ branched chain hydroxybenzoate and/or C12, C16, C18 branched chain benzoate stabilizers/solubilizers |

Despite these advances, there is still a huge need and demand for photo-stabilizers that are able to stabilize photosensitive ingredients used in and within foods, cosmetics, personal care and household products that are more effective and more forgiving than the aforementioned compounds. The shortcomings of presently available photostabilizers include, but not limited to:

Hydrolytic instability most likely arising from the presence of one or more ester functionalities, the later limiting their use in basic pH compositions/conditions. Also, esters in general are more hydrolytically unstable than their non-ester counter parts, for example ketones, Presence of color and formation of intense yellow/orange coloration in basic pH due to the presence of phenolic hydroxyl group or groups. Non-phenolic stabilizers are also highly colored, for example, Octocrylene and octocrylene derivatives, namely, Polycrylene® (Viscous oily liquid, Polyester-8, available from Hallstar), Solastay™ $S_1$ (Viscous oily liquid, Ethylhexyl methoxycrylene, available from Hallstar).

Indications of contact allergy (CA) and photocontact allergy (PCA) to Octocrylene, a widely used UV-B organic sunscreen and an excellent stabilizer of Avobenzone.

Loss of effectiveness when exposed to UV dose of >40 Joules/cm², as found with, for example, Corapan® TQ (Diethylhexyl 2,6 naphthalate, Symrise), Oxynex® ST (Diethyhexyl syringylidene malonate, EMD Chemicals), Instability of photostabilizers having phenolic functionality in basic pH due to the formation of phenolate anion.

SUMMARY OF THE INVENTION

Surprisingly, it has now been found that certain derivatives of 2,4-pentanedione compounds without having phenolic hydroxyl are very effective in stabilizing photosensitive ingredients present within cosmetics, personal care and household products, providing many, if not most, of the desired attributes of the utopian, or nearly utopian, cosmetics, personal care and household product compositions.

Specifically, according to the present invention there are provided new benzylidene 2,4-pentanediones according to the Formula I as follows:

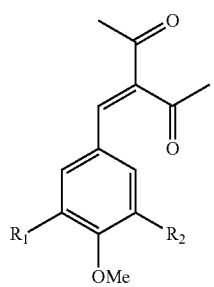

Formula I wherein $R_1$ and $R_2$, which may be the same or different, are independently H, alkyl or alkoxy, preferably H, alkyl or alkoxy, wherein the alkyl or alkoxy groups are linear or branched and have from 1 to 8 carbon atoms, preferably from 1 to 6 carbon atoms, most preferably from 1 to 4 carbon atoms and wherein Me is most preferably methyl, but can also be a linear or branched lower alkyl of from 2 to 8 carbon atoms, Preferred compounds according to Formula I are those wherein $R_1$=H and $R_2$=H or an alkyl or alkoxy group of from 1 to 8, preferably from 1 to 6, most preferably from 1 to 4 carbon atoms or wherein $R_1$=$R_2$. Especially preferred compounds are those wherein $R_1$=$R_2$=H; $R_1$=H and $R_2$=CH$_3$; $R_1$=$R_2$=CH$_3$; $R_1$=OCH$_3$ and $R_2$=H; and $R_1$=$R_2$=OCH$_3$. The presence of the two acetyl groups at the C-3 position of the pentadedione function of the compounds according to the present teaching is critical for proper and efficaceous stability. The presence of just a single acetyl group at this position results in poor, if any, stability. For example, Dehydrozingerone methylether (Vanillylidene acetone methyl ether, Formula II), a compound that is synthetically obtained by reacting Vanillin methyl ether and acetone, has just the single acetyl group a the C-3 position and fails to stabilize photosensitive compounds, as demonstrated in the experimental section below,

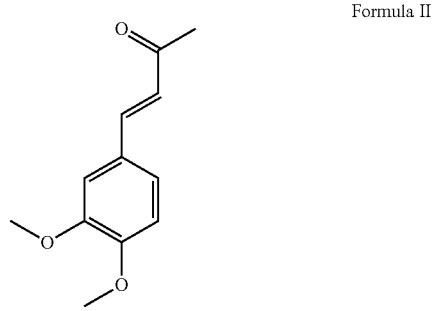

Formula II

According to a second aspects of the present invention there are provided methods of improving the overall stability of photosensitive ingredients used in foods, cosmetics, personal care and household products as well as the overall stability of the foods, cosmetic, pharmaceutical/medicinal, personal care, household and agrichemical products into which such photosensitive ingredients are incorporated which method comprises the addition of the compounds according to Formula I to the photosensitive ingredients or to the products in which said photosensitive ingredients are added.

According to a third aspect of the present invention there are provided photo-stabilized additives for food, cosmetic, personal care and household products as well as photostabilized food cosmetic, personal care and household products comprising said additives according to Formula I.

DESCRIPTION OF THE INVENTION

Given the broad applicability of the teachings of the present specification, it is not possible to discuss each and every application, and certainly not in any detail. Rather, the following specification, while mentioning a number of specific applications, is primarily focused on sunscreen compositions and formulations; though, again, these teachings are applicable to any number of cosmetic, skin care, health and beauty aid products, including personal cleansing products such as soaps, shampoos, gels, etc., as well as food, household cleaning, sanitizing, odor control, etc., products generally. Additionally, Applicant oftentimes indicates that these products "may" include various constituents or that the stabilizing compounds "may" be used in certain systems. In this regard, the word "may" is employed in various contexts to indicate that it can or is able to be so used and/or that it is an optional use. Similarly, Applicant makes numerous statements as to his "belief" with respect to the functionality and applicability of the claimed compounds and their use. In this context, it is to be understood that this expression is not to be misconstrued as a uncertainty as to the scope of the invention, but a recognition, in light of its broad scope, that it is not feasible to test each and every possible application or to present the same in a limited patent specification. Consequently, based on the work that has been done and the teaching that has been provided, it is Applicant's full expectation that these "beliefs" are not suppositions or theory, but affirmative statements of utility and applicability. Finally, Applicant speaks of the "present invention" and of the "invention" generally, as used herein, it is understood that this term is not limited to that which is claimed, but refers to the overall teachings of this specification as well as the extrapolation thereof as would be understood and appreciated by those skilled in the art.

According to the present invention there are provided new compounds that are suitable as stabilizers, especially photo-stabilizers, for use in the stabilization of various ingredients used in food, cosmetic, personal care, medicinal/pharmaceutical, household, and agrichemical products as well as in the stabilization of the food, cosmetic, personal care and household products into which such ingredients are incorporated. These compounds, which are identified as corresponding to Formula I below, may be incorporated into the ingredients themselves in order to provide enhanced stabilization to them prior to their incorporation into their final product formulations, into the final product formulations into which such ingredients are incorporated, or both. In the latter instance, a stabilizingly effective amount of a compound according to the present teaching is added to the ingredient itself to provide stabilization to that ingredient during storage and use and an additional amount of the same or a different compound according to Formula I is added to the product into which such additive is incorporated to provide further stabilization to the final products. In addition to the foregoing stabilizing effect, these compounds also provide transition metal chelating activity. Specifically, these compounds are capable of chelating transition metals, such as iron, copper, etc., which are known to affect, if not catalyze, free-radical generation and/or reactions. Free radicals are known to have adverse biomolecular effects, especially in the skin. For example, transition metals are known to influence if not catalyze the Fenton reaction, generating highly toxic hydroxyl radicals leading to biomolecular damage. Thus, the compounds of Formula I not only provide enhanced stability and efficacy to the ingredients and products, including skin care products, into which they are incorporated, but also provide a direct benefit to the skin itself by further protecting skin from damage due to UV light, including UV light induced transition metal free radical generation and its subsequent oxidative stress and other damaging effects on skin.

The new stabilizer compounds according to the present invention are generally classified as benzylidene substituted 2,4-pentanediones and have the general Formula I as follows:

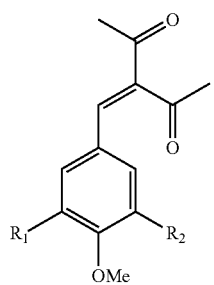

Formula I wherein $R_1$ and $R_2$, which may be the same or different, are independently H, alkyl or alkoxy, preferably H, alkyl or alkoxy, wherein the alkyl or alkoxy groups are linear or branched and have from 1 to 8 carbon atoms, preferably from 1 to 6 carbon atoms, most preferably from 1 to 4 carbon atoms and wherein Me is most preferably methyl, but can also be a linear or branched lower alkyl of from 2 to 8 carbon atoms. Preferred compounds according to Formula I are those wherein $R_1$=H and $R_2$=H or an alkyl or alkoxy group of from 1 to 8, preferably from 1 to 6, most preferably from 1 to 4 carbon atoms or wherein $R_1$=$R_2$. Especially preferred compounds are those wherein $R_1$=$R_2$=H; $R_1$=H and $R_2$=$CH_3$; $R_1$=$R_2$=$CH_3$; $R_1$=$OCH_3$ and $R_2$=H; and $R_1$=$R_2$=$OCH_3$.

Theses compounds may be prepared by various methods but are most conveniently prepared by reacting a benzaldehyde with acetyl acetone in the presence of a suitable catalyst and reaction medium, preferably piperidine and cyclohexane, at reflux temperature under continuous azeotropic water removal. The benzaldehyde reactant will be that which corresponds to the desired substitution of the benzylidene derivative of the final benzylidene pentanedione. The crude product resulting from the foregoing reaction may then be purified by crystallization with methanol to produce the desired benzylidene 2,4-pentanedione. Suitable reactions and reaction conditions are set forth in the examples contained herein.

Surprisingly, it has now been found that the compounds according to Formula I above are efficacious as stabilizers for use with a wide variety of compounds, ingredients and the like that are otherwise unstable owing to photo-instability, heat instability, and the like. In particular, the compounds of the present invention are found to provide photo-stability protection to a broad variety of otherwise unstable, especially photo-unstable, compounds used as ingredients in food, cosmetic, personal care, medicinal/pharmaceutical, household, and agrichemical products as well as to food, cosmetic, personal care, medicinal/pharmaceutical, household, and agrichemical products in general, particularly those into which such photo-unstable ingredients are incorporated. For purposes of convenience, and because the primary action of the compounds of the present invention is photo-stabilization, all reference to instability shall henceforth be discussed in terms of photo-instability and photo-stability; though it is to be appreciated that all forms of stabilization, whether heat, air, light, etc., manifested by the compounds of the present invention are contemplated and intended. Furthermore, it is to be appreciated that a single compound may be used or one may use a combination of two or more compounds according to Formula I. Furthermore, it is to be appreciated that the compounds of Formula I may also be used in combination with one or more conventional antioxidants and/or stabilizers, and that such combinations oftentimes results in a synergy as between the conventional antioxidant and/or stabilizer.

While it is believed that all compounds according to Formula I above are suitable and efficacious, it is to be understood that the present invention is especially directed towards those compounds according to Formula I above that are capable of reducing the degradation of photosensitive compounds which absorb visible light or UV rays to form high energy chromophores, especially those that form unstable chromophores once exposed to visible light and/or UV radiation. Accordingly, photosensitive compounds or compositions that are only exposed to visible light, or substantially or predominantly only to visible light, for example, during storage in a warehouse, on a shelf in a store or in a home, are protected by the incorporation therein of the compounds according to Formula I above. Furthermore, protection continues even when protected compounds by the methods of the invention are exposed to natural sunlight that contains both UV and visible light.

The amount by which the compounds according to the present invention are incorporated into the ingredients and/or the final products will vary depending upon the instability of the ingredient compounds and/or the products themselves; but in any event, the amount will be a photostabilizingly effective amount, i.e., an amount that enhances the stability of the ingredients and/or final compositions as compare to those without the compounds according to the present invention. Generally speaking the amount will be from about 0.001 to about 15, preferably from about 0.5 to about 5, weight percent based on the weight of the photo-unstable ingredient(s) where the additive according to the present invention is added to the ingredient itself for stability thereto, especially for stability prior to its incorporation into a final or intermediate product. In the case of intermediate and/or final products which incorporate such photo-sensitive ingredients, the amount by which the compounds according to Formula I above are incorporated will be from about 0.01 to about 15, preferably from about 0.1 to about 10, most preferably from about 0.5 to about 5 weight percent based on the weight of the total composition, whether an intermediate composition or a final product. Where combinations of two or more compounds according to Formula I above are used, the combined amounts of their use will still generally fall within the above defined ranges, though somewhat higher levels may be used depending on the desired end performance.

While it is believed that the compounds according to the present invention will provide stability, especially photo-stability protection to photosensitive compounds and compositions generally, the compounds of the present invention are especially suitable for use with those photosensitive compounds (ingredients) used in food, cosmetic, personal care, medicinal/pharmaceutical, household, and agrichemical products as well as such products which incorporate photosensitive and/or oxidation prone compounds/ingredients. Of course, theses categories overlap to an extent as the industry does not have defined cross-market definitions; however, those skilled in the art will readily appreciate the broad applicability and intended scope of the teachings herein and of the appended claims hereto. In following, the following paragraphs describe many of the ingredients and compositions which benefit from the incorporation of the compounds according to Formula I above, but are not intended to be exclusive or limiting. For the sake of simplicity and given the broad scope of the intended and expected applicability of the present teaching, the following is intended as exemplary of the applications to which these compounds may be used and not limiting.

It is well known that a wide range of aromatic compounds when exposed to UV or visible light generate excited states that can undergo rapid and efficient energy transfer in oxygen to give singlet oxygen. Energy transfer to yield singlet oxygen usually competes with electron transfer, consequently many photosensitizers give both singlet oxygen and super oxide anion. The yield of singlet oxygen versus super oxide anion is therefore dependent on the sensitizer, the excitation wavelength, and the reaction conditions. It has now been found that compounds according to Formula I above are also good quenchers for singlet oxygen thereby providing improved stabilization of formulation ingredients, particularly those that are photosensitive. Literature data shows that singlet oxygen is also responsible for degrading Avobenzone (R K Chaudhuri, et al., Design of a photo stabilizer having built-in antioxidant functionality and its utility in obtaining broad-spectrum sunscreen formulations, Photochemistry and Photobiology, 82:823-828, 2006). Further improvement in stabilization can be obtained by combining the present inventive compounds with antioxidants having strong singlet oxygen and or superoxide quenching ability. In this regard, many traditional sunscreen additives can be combined with compounds according to the present invention to stabilize non-sunscreen compositions such as polymers, colors/colorants, fragrances and flavoring ingredients. This is particularly so where the absorption properties, i.e., absorption wavelength, of the traditional sunscreen additive coincides or overlaps with the absorption properties of the compound according to Formula I.

Other combinations are possible as well. For example, trans-Urocanic acid is a major chromophore of singlet oxygen (K M Hanson, J D Simon, "Epidermal trans-Urocanic acid and the UV-A-induced photoaging of the skin", Proc Natl Acad Sci USA, 95:10576-10578, 1998; J D Simon, "Spectroscopic and dynamic studies of the epidermal chromophores trans-urocanic acid and eumelanin", Ace Chem Res, 33:307-313, 2000). It is also present at high concentrations in the upper epidermis and stratum corneum. Trans-Urocanic acid (3-(1H-imidazol-4(5)-yl)-2-propenoic acid) is a metabolite of histidine and a substantial constituent of the stratum corneumn, making up 0.7% of the dry weight of the epidermis (T Mohammad, H Morrison and H. HogenEsch, "Urocanic acid photochemistry and photobiology", Photochem Photobiol, 69:115-135, 1999). Thus, it is believed that the compound according to Formula I above wherein $R_1$=$OCH_3$ and $R_2$=H is a good photostabilizer/light-absorbing stabilizer for skin care, especially sunscreen, products acting against photo-induced singlet oxygen from the trans-Urocanic acid pathway.

This combined "boosting effect" observed with combinations of singlet oxygen quencher and the compounds of Formula I not only provides product stabilization effects beyond what was previously possible, but also offers synergistic, cost-effective solutions of product stabilization and skin protection as an added advantage. Furthermore, it is to be appreciated that this synergy is not limited to combinations with antioxidants but is applicable to combinations with stabilizers in general. Indeed, the compounds of Formula I may be used beneficially in combination with conventional antioxidants and stabilizers employed in food, cosmetic, personal care, medicinal/pharmaceutical, household, and agrichemical products as well as in stabilizing the additives and actives therefore prior to their use in making such products.

It is well known that many ingredients used on in food, cosmetic, personal care and household products are not always photochemically stable. This instability omits their utility, both in terms of the products into which they are incorporated as well as the variety and scope of products into which they could be incorporated but for their instability. Similarly, many other compounds and compositions that could be used as ingredients in such products are not used because of theft instability. This is especially so for, though not limited to, polyunsaturated and aromatic compounds. Examples of such ingredients include sunscreen actives, colorants, dyes, antioxidants, flavors, fragrances, vitamins, pharmacological actives, and the like. More specific examples, as will be discussed in further detail below, include avobenzone, carotenoids, tocopherols, retinol, retinoic acid, retinaldehyde, guaiazulene, vanillin and menthylanthranillate. Additionally, many polymers having no un-saturation, especially those used as thickening agents in cosmetics or personal or household products, are also susceptible to degradation under heat, sun light or extended storage in room temperature due to free radical formation under these conditions resulting in the drop in the viscosity. In this regard, it is to be appreciated that the stabilization effect of the compounds of Formula I are not limited to photostabilization. Indeed, these compounds may and do provide enhanced stabilization from heat, oxidation, and other forms of instability and/or degradation resulting from environmental factors as well as the general aging of the ingredients themselves, e.g., inherent free radical generation.

One class of photosensitive ingredient that may benefit from the use of the stabilizer compounds according to Formula I above are those compounds/compositions typically referred to as vitamins and their derivatives: all of which are generally regarded as being subject to photo-degradation. Vitamins and vitamin derivatives include, for example, vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C and derivatives (for example ascorbyl palmitate, magnesium ascorbyl phosphate, ascorbyl acetate), vitamin D, ergocalciferol (vitamin $D_2$), vitamin E, DLα-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$). Preferred vitamins are, for example, vitamin A palmitate, vitamin C and derivatives thereof, DLα-tocopherol, tocopherol E acetate, nicotinic acid, pantothenic acid and biotin. Vitamin E, which is often added to cosmetic products and personal care products is also preferably stabilized by the compounds according Formula I. These compounds are also especially suited for use in the stabilization of Vitamins C and K and derivatives thereof.

Other common ingredients for food, cosmetic, personal care and household products that are subject to photo-instability and which will benefit from the present invention are the oils and waxes, including natural and synthetic oils and waxes. Natural waxes include, for example, carnauba wax, candelilla wax, rice bran wax, bees wax, lanolin, motan wax and ceresine wax. Synthetic waxes, typically derived from hydrocarbons, include, for example, paraffin wax, microcrystalline waxes, lauric acid, myristic acid, palmitic acid, stearic acid, behenic acid, sorbitane fatty acid, and the ester and amide derivatives thereof. Mixtures of waxes can also be stabilized. Natural oils include, for example, coconut oil, canola oil, soybean oil, rapeseed oil, palm kernel oil, murumuru tallow, and tucum oil. Generally speaking, natural waxes and oils mean any wax or oil derived from plant or animal material including, but not limited to, waxes and oils that are derived from plants that have been genetically modified either through traditional breeding or through genetic engineering techniques.

Poly-unsaturated color compounds which are not photochemically stable and which benefit from the stabilizing effect of the compounds of Formula I include, for example, carotenoids, Ubiquinones and Azulenes such as guaizulene. Guaiazulene has very limited photostability as almost 90% of Guaiazulene is lost due to degradation when exposed to a solar simulator at a total energy of 100 $mJ/cm^2$ Similarly, β-carotene is even more unstable as it degrades when stored at room temperature in ambient light. Other photosensitive caroteniods include Lycopene, Zeaxanthine, Cantaxanthine, α, β, γ, δ-Carotenes, Astacin, Astaxanthin, Chrysanthemaxanthin, Torularhodin, Violaxanthin, Capsanthin, and Capsorubin, among others. Photo-sensitive Azulenes include Azulene, Guaiazulene, and Guaiol, among others. Photosensitive Ubiquinones (Coenzyme Q) include various compounds whose structures are based on or derived from the 2,3-dimethoxy-5-methyl-benzoquinone nucleus with a variable terpenoid side chain containing one to twelve mono-unsaturated trans-isoprenoid units. Such compounds with ten units are the most common in animals. These Ubiguinones are generally characterized as Coenzyme $Q_n$ in which n is 1 to 12: the most naturally occurring members being the Coenzymes $Q_6$ to $Q_{10}$.

Another class of compounds that benefit from the use of the compounds according to Formula I above are the tocopherols, especially natural tocopherols. Tocopherols are a mixture of four lipid-soluble tocopherols (α, β, γ, δ) and four lipid-soluble tocotrienols (α, β, γ, δ). Tocopherols and tocotrienols differ only in their phenyl side chain. The chromanol head of each is identical with α, β, γ, δ-isomers, each containing an essential hydroxyl group necessary for antioxidant activity. Synthetic DL-Tocopherols or its derivatives, like acetate, succinate, etc. are also included. Photochemically, tocopherols (synthetic or natural) are not very stable (R K Chaudhuri, Phyllanthus tannins, in P Elsner and H I Maibach, eds. Cosmeceuticals: Drugs vs Cosmetics, Volume 27, New York, Taylor and Francis, p. 465, 2005).

The photoinstability of organic peroxides is well known: indeed, it is this instability that is counted on for certain applications such as in the initiation and/or activation of, for example, free radical polymerization. However, organic peroxides also serve as useful ingredients in various foods, cosmetic, personal care and/or household products, and—uses where such photoinstability is less desirable, if not undesirable. For example, benzoyl peroxide is used in pharmaceutical and consumer products as an active ingredient for therapeutic treatments. Thus, when organic peroxides are used for purposes other than free radical initiation, it is desirable that the organic peroxide, and the composition in which it is present, be as stable as possible since instability is problematic, leading to reduced efficacy of the properties for which it is employed, if not loss of the active itself, as well as shortened shelf lives, required expiration dating, higher product costs, special storage considerations, and/or product returns.

Yet another class of ingredient compounds and compositions that are photosensitive and which benefit for the stabilizing effect of the compounds of Formula include colorants, dyes and/or organic pigments. These ingredients may be naturally derived or synthetic and include, for example, Annatto (Bixin), Anthocyanin, Beta-carotene, Betanin, Capsanthin/capsorubin, Chlorophyll, Crocetin, Curcumin, and Luteolin. Natural colors are typically extracted from plants and are responsible for the coloration of such plants. One group of natural colors are the curcuminoids. Curcuminoids are polyphenolic pigments found in the spice turmeric. Curcuminoids are responsible for the yellow color of turmeric, as well as the yellow color of curry. The major curcuminoids are curcumin, demethoxycurcumin and bisdemethoxycurcumin. These substances are most often extracted from *Curcuma longa*: a tropical plant native to south and southeast tropical Asia and a member of the ginger or Zingiberaceae family. They typically comprise from form 3 to 6% of the *Curcuma longa* plant, 70 to 75% of which is curcumin, 15 to 20% demethoxycurcumin, and about 3% bisdemethoxycurcumin. Other Curcuminoids include Cassumunin A and Cassumunin B, isolated from tropical ginger, Zingiber cassumunar. Yet another group of natural ingredients are the aryl ketones which are photosensitive, especially dehydrozingerone, obtained from Ginger. The rhizome of Zingiber officinalis, one of the most widely used species of the ginger family, is a common condiment for various foods and beverages.

Other organic color agents that can be photostabilized by the use of the compounds of Formula I include, for example, reds (D&C Red #6 Barium Lake, D&C Red #6, D&C Red #7, D&C Red #21, D&C Red #22, D&C Red #27, D&C Red #28, D&C Red #30, D&C Red #33 Aluminum Lake, D&C Red #34 Calcium Lake, D&C Red #36, and FD&C Red #40 Aluminum Lake), orange (D&C Orange #5), yellows (FD&C Yellow #5 Aluminum Lake, FD&C Yellow #6 Aluminum Lake, FD&C Yellow #10 Aluminum Lake), and blue (FD&C Blue#1 Aluminum Lake).

Various inorganic coloring or color inducing compounds are also subject to photodegradation and can be stabilized against this degradation by the compounds of Formula I. Exemplary inorganic coloring and color inducing compounds include the iron oxides, including yellow oxide ($Fe_2O_3H_2O$); Red Oxide, the anhydrous form of Yellow Oxide ($Fe_2O_3$) and Black Oxide ($FeOFe_2O_3$). Other inorganic compounds include ferric ammonium ferrocyanide ($Fe(NH_4)Fe(CN)_6.nH_2O$); Manganese violet, a manganese ammonium pyrophosphate complex, ($Mn(NH_4)P_2O_7$); Ultramarine blue, a complex sodium aluminum sulfo-silicate whose intense color is a result of the sulfide linkages which are present in a highly resonant state ($Na_7Al_6O_{24}S_3$); and the Chrome oxide greens, chromium sesquoxide ($Cr_2O_3$) and the hydrated chromium sesquioxide ($Cr_2O_3.nH_2O$).

A listing of approved colorants (except hair colors) that can be stabilized by the compounds of Formula I are found in U.S. Food and Drug Administration color additive regulations, 21 CFR 73 and 74 and in Annex IV of the EC Cosmetics Directive 76/768/EEC. Exemplary colorants found in these sources include, for example, Acid Black 1, Acid Black 52, Acid Blue 3, Acid Blue 9, Acid Blue 9 Aluminum Lake, Aka223, Chromium Oxide Greens, Acid Blue 9 Ammonium Salt, Acid Blue 62, Acid Blue 74, Acid Blue 74 Aluminum Lake, Acid Green 1, Acid Green 25, Acid Green 50, Acid Orange 6, Acid Orange 7, Acid Red 14 Aluminum Lake, Acid Red 18, Acid Red 18 Aluminum Lake, Acid Red 27, Acid Red 27 Aluminum Lake, Acid Red 33, Acid Red 51, Acid Red 73, Acid Red 87, Acid Red 92, Acid Red 95, Acid Red 184, Acid Red 195, Acid Violet 9, Acid Violet 43, Acid Yellow 3, Acid Yellow 3 Aluminum Lake, Acid Yellow 23, Acid Yellow 23 Aluminum Lake, Acid Yellow 73, Basic Blue 6, Acid Yellow 73 Sodium Salt, Acrylic Resin Coated Aluminum Powder, Aka2, Aka3, Aka102, Aka104(1), Aka105(1), Aka106, Aka201, Aka202, Aka203, Aka204, Aka205, Aka206, Aka207, Aka208, Aka213, Aka214, Aka215, Aka218, Aka219, Aka220, Aka221, Aka22, Aka225, Aka226, Aka227, Aka228, Aka230 (1), Aka230(2), Aka231, Aka232, Aka401, Aka404, Aka405, Aka501, Aka502, Aka503, Aka504, Aka505, Aluminum Laccate, Aluminum Powder, Aluminum Stearate, Annatto, Anthocyanins, Ao1, Ao2, Ao201, Ao202, Ao203, Ao204, Ao205, Ao403, Ao404, Astaxanthin, Basic Blue 6, Basic Blue 41, Basic Yellow 11, Beetroot, Bismuth Oxychloride, Blue 1, Blue 1 Lake, Blue 4, Brilliant Black 1, Bromocresol Green, Bromothymol Blue, Bronze Powder, Brown 1, Calcium Ferrite, Calcium Stearate, Capsanthin/Capsorubin, Caramel, Carbon Black, Carmine, Beta-Carotene, Carotenolds, Chlorophyllin-Copper Complex, Chromium, Chromium Hydroxide Green, Cobalt Aluminum Oxide, Cochineal, Copper Powder, Crocus Sativus Rower Extract, Curry Red, Daidai201, Daidai203, Daidai204, Daidai205, Daidai206, Daidai207, Daidai401, Daidai402, Daidai403, Dihydroxyacetone, Direct BLue 86, Disodium EDTA-Copper, Dunaliella Bardawil Powder, Epoxy Resin Coated Aluminum Powder, Erythrulose, Ext, Violet 2, Ext, Yellow 7, Ext. Yellow 7 Lake, Fast Green FCF, Ferric Ammonium Citrate, Ferric Ammonium Ferrocyanide, Ferric Ferrocyanide, Fluorescent Brightener 230, Fluorescent Brightener 236, Gardenia Florida Extract, Gold, Green 3, Green 3 Lake, Green 5, Green 6, Green 8, ne, Guanine, Haematococcus Pluvialis Powder, Haematoxylon Campechianum Wood Extract, Henna, Iron Oxides, Katsu201, Ki4, Ki5, Ki201, Ki202(1), Ki202(2), Ki203, Ki204, Ki205, Ki401, Ki402, Ki403(1), Ki404, Ki405, Ki406, Ki407, Kuro401, Lactoflavin, Lawsone, Magnesium Stearate, Manganesa Violet, Mica, Midori3, Midori201, Midori202, Midori204,k Midori205, Midori402, Murasaki201, Murasaki401, Natural Red 26, Ninhydrin, Orange 4, Orange 4 Lake, Orange 5, Orange 5 Lake, Orange 10, Orange 10 Lake, Orange 11, Oxobenzoxazinyl Naphthalene Sulfoanilide, Pigment Blue 15:2, Pigment Green 7, Pigment Orange 5, Pigment Red 4, Pigment Red 5, Pigment Red 48, Pigment Red 53, Pigment Red 53:1, Pigment Red 57, Pigment Red 57:1, Pigment Red 63:1, Pigment Red 64:1, Pigment Red 68, Pigment Red 83, Pigment Red 88, Pigment Red 90:1 Aluminum Lake, Pigment Red 112, Pigment Red 172 Aluminum Lake, Pigment Red 173 Aluminum Lake, Pigment Red 190, Pigment Violet 19, Pigment Yellow 1, Pigment Yellow 3, Pigment Yellow 12, Pigment Yellow 73, Ponceau SX, Pyrophyllite, Red 4, Red 4 Lake, Red 6, Red 6 Lake, Red 7, Red 7 Lake, Red 17, Red 21, Red 21 Lake, Red 22, Red 22 Lake, Red 27, Red 27 Lake, Red 28, Red 28 Lake, Red 30, Red 30 Lake, Red 31, Red 31 Lake, Red 33, Red 33 Lake, Red 34, Red 34 Lake, Red 36, Red 36 Lake, Red 40, Red 40 Lake, Silver, Sodium 5-Nitroguaiacolate, Sodium Zinc Cetyl Phosphate, Solvent Green 3, Solvent Green 7, Solvent Orange 1, Solvent Red 1, Solvent Red 3, Solvent Red 23, Solvent Red 24, Solvent Red 43, Solvent Red 48, Solvent Red 49:1, Solvent Red 72, Solvent Red 73, Solvent Violet 13, Solvent Yellow 18, Solvent Yellow 29, Solvent Yellow 33, Solvent Yellow 44, Sunset Yellow, Sunset Yellow Aluminum Lake, Titanium Dioxide, Titanium Oxynitride, Titanium/Titanium Dioxide, Ultramarines, Umber, Vat Red 1, Violet 2, Yellow 5, Yellow 5 Lake, Yellow 6, Yellow 6 Lake, Yellow 7, Yellow 7 Lake, Yellow 8, Yellow 10, Yellow 10 Lake, Yellow 11, Yellow Ocher; Zinc Oxide, Zinc Stearate.

Fragrance ingredients are another class of compounds that are prone to degradation and instability and which benefit from the stabilizing effect of the compounds of Formula I., Such compounds and ingredients include, for example: Abbarome® 011, Acalea, Allyl Amyl Glycolate, alpha-Terpineol, Alpha Pinene, Ambrettolide, Amyl Cinnamic Aldehyde, Amyl Phenyl Acetate, Amyl Salicylate, Andrane, Anethole 21/22, Anethole USP, Anethole USP, Aphermate, Apo Patchone, Bacdanol®., Benzyl n-Butyrate, Benzyl Propionate, Benzyl Salicylate, Bergamal, Beta Naphthyl isobutyl Ether, Beta Pinene Coeur, Bicyclononalactone, Bomafix™ Canthoxal, Cashmeran®., Cedrafix, Cedramber®., Cedrenyl Acetate Chinese, Celestolide, Cinnamalva, cis-3-Hexenyl Salicylate, Citral Dimethyl Acetal, Citralva®., Citronalva, Citronellol 700 98TA, Citronellol 750, Citronellol 950, Citronellol Coeur, Citronellyl Acetate, Citronellyl Acetate A, Citronellyl Acetate Pure, Citronellyl Formate, Clarycet, Clonal, Coniferan, Cyclabute, Cycacet™, Cyclaprop™ Cyclemone A, Cyclogalbaniff, Cyclohexyl Ethyl Acetate, Cyclohexyl Ethyl Alcohol, Damascol 4, Decyl Methyl Ether, Delta Damascene, Dihydro Cyclacet, Dihydro Floralate, Dihydro Floralol, Dihydro Myrcenyl Acetate, Dihydro Terpineol, Dihydro Terpinyl Acetate, Dihydro Terpinyl Acetate DSA, Dimethyl Benzyl Carbinol, Dimethyl Benzyl Carbinyl Acetate, Dimethyl Benzyl Carbinyl Butyrate, Dimethyl Cyclormol, Dimethyl Octanol-PQ, Dimethyl Phenyl Ethyl Carbinyl Acetate, Dimyrcetol, Diola, Dipentene 5100, Dulcinyl®. Recrystallized, Ethyl 3 Phenyl Glycidate, Ethyl Ortho Methoxy Benzoate, Fleuramone, Fleuranil, Floralate, Floralol, Floralozone, Fraistone, Fructone, Galaxolide®. 50 BB, Galaxolide®. 50 DEP, Galaxolide®. 50 DPG, Galaxolide® 50 IPM, Galbanum Coeur, Gelsone, Geraldehyde, Geraniol 5020, Geraniol 7030., Geraniol 980, Geraniol Coeur, Geranyl Acetate, Geranyl Acetate Extra, Geranyl Acetate Pure, Grisalva, Guaiyl Acetate, Helional®., Herbac, Hexadecanolide, Hexylon, Hexyl Acetate, Hexyl Cinnamic Aldehyde, Hexyl Salicylate, Hyacinth Body, Hyacinth Body No. 3, Hydratropic Aldehyde Dimethyl Acetal, Hydroxyol, Hypo-Lem, Indolarome, Indolene 50, Intreleven Aldehyde, Intreleven Aldehyde Special, Ionone 100%, Ionone Alpha, Ionone Alpha Beta, Regular, Ionone Beta, Iso Amyl Butyrate, Iso Bornyl Propionate, Iso Butyl Quinoline, iso E Super®, Isoamyl Salicylate, Isobutyl Phenyl Acetate, Isocyclemone E, Isocyclocitral, Isocyclogeraniol, Isoproxen, Jasmal, Jasmelia, Jessemal™ Kharismal, Koavone®., Kohinool®., Lavonax, Lemsyn, Liffarome, Lindenol®., Lymolene, Lyral®, Lyrame, Lyrame Super, Maritima, Melafieur, Methyl Anthranilate, Methyl Cedryl Ketone Chinese, Methyl Cinnamic Aldehyde alpha, Methyl Ionone Gamma A, Methyl Ionone Gamma Coeur, Methyl Ionone Gamma Pure, Methyl Lavender Ketone, Muguesia, Muguet Aldehyde 50, Muguet Aldehyde 50 BB, Myrac Aldehyde, Myrcenol Super, Myrcenyl Acetate, Neoproxen, Neral 800, Neral 850, Neral 900, Neryl Acetate, Ocimene, Ocimenyl Acetate, Octacetal, Orange Rower Ether, Orivone, Orriniff 25% IPM, Oxaspirane, Ozofleur, Pamplefleur®., Peomosa, Phenafleur, Phenoxanol®, Phenoxyethyl Isobutyrate, Phenoxyethyl Propionate, Phenyl Ethyl Acetate, Phenyl Ethyl Alcohol, Phenyl Ethyl Benzoate, Phenyl Ethyl Formate, Phenyl Ethyl Isobutyrate, Phenyl Ethyl Phenyl Acetate, Phenyl Ethyl Salicylate, Piconia, Precyclemone B, Prenyl Acetate, Proflora, Pseudo Linalyl Acetate, Reseda Body, Rosalva, Rosamusk, Roseate, Rosemarel, Salicynalva, Sanjinol, Santaliff, Spirodecane, Strawberiff®, Styrallyl Propionate, Syvertal, Terpineol 900, Terpineol Extra, Terpinolene 20, Terpinolene 90, Terpinolene 90 PQ, Terpinyl Acetate (CST), Terpinyl Acetate (GUM), Tetrahydro Geraniol, Tetrahydro Muguol, Tetrahydro Muguol Coeur, Tetrahydro Myrcenol, Tetrarneran, Tobacarol, Trimofix®. O, Triplain™, Triplal™ Extra, Unipine 60®, Unipine 759, Unipine 80®, Unipine 85®, Unipine 90®, Unipine NCL®., Unipine S-70®, Unitene D®, Unitene LP®., Unitene WST®, Vander B, Vanoris, Verdol, Verdox™, Verdox™ HC, Verdural B Extra, Verdural Extra, Vernol®, Vertenex®, Vertenex® HC, Vertofix® Coeur, Vigoflor, and Violiff. Of these, the more commonly used fragrance ingredients are, for example, Muguet Aldehyde 50, Myrac Aldehyde, Phenyl Ethyl Formate, Precyclemone B. Syvertal, Strawberiff®, and Triplal™.

Flavor ingredients susceptible to degradation and instability which benefit from the stabilizing effect of the compounds of Formula I. include a multitude of synthetic and natural compounds and compositions, and especially include the essential oils. The INCI Dictionary includes more than 100 essential oils, only a few of which are mentioned here for simplicity sake, including Basil, Bergamot, Black Pepper, Cedarwood, Chamomile, Cinnamon, Clary Sage, Clove, Coriander, Cypress, Eucalyptus, Fennel, Geranium, Ginger, Grapefruit, Jasmine, Juniper, Lavender, Lemon, Lemongrass, Melaleuca or Tea Tree, Myrrh, Olibanum, Patchouli, Peppermint, Rose, Rosemary, Rosewood, Sage, Sandalwood, and Thyme. Examples of other flavor ingredients include 4,5-Dimethyl-2-ethyl-3-thiazoline, 6-Methyl Coumarin, Allyl Caproate, Anethole USP, Asafoetida Oil English Distilled SAS, Black Pepper, Black Pepper, Black Pepper Oil, Black Pepper Oil English Distilled SAS, Buchu Sulfur Fractions, Butyric Acid, Cardamon Oil English Distilled SAS, Cassia Oil, Cassia Oil Redistilled, Cinnamon Bark Oil, Cinnamon Leaf Oil Cleaned, Clove Bud Oil English Distilled SAS, Clove Leaf Oil Cleaned, Clove Leaf Oil Redistilled, Cocain™, Cocoa Distillate (Nat.), Cocoa Essence Dark, Cocoa Essence White, Cocoa Extract Nat., Coffee Enhancer Base, Coffee Enhancer W/S, Coffee Extract, Coffee Extract Italian Roast M3881 Nat., Coffee Extract Nce Iiim Nat., Coffee Extract Nce Iv Nat., Coriander Oil, Cyclodithalfarol-705, delta Decalactone, Dimethyl Benzyl Carbinyl Butyrate, Dimethyl Sulfide, Dithione 865, Ethyl-2-Methyl Butyrate, Ethyl-3-Hydroxy Butyrate, Ethyl Butyrate, Ethyl Iso Butyrate, Ethyl Iso Valerate, Ethyl Oxanoate 369, Eucalyptus OH 80%, Farnesene 1% PG/ETOH, Furfurrole 302, gamma-Decalactone, gamma-Hexylactone, gamma-Octalactone, gamma Dodecalactone, Ginger OH Chinese, Ginger Oil Nigerian English Distilled SAS, Grapefruit Key, Grill Flavor 013, Grill Flavor W/D, Heptan-2-One (Nat.), Hexene-3-One-4, Hexyl Acetate, Homo Cyclocitral, beta, Honey Distillate Nat., Ionone Beta, Iso Amyl Iso Valerate, Iso Butyl Caproate, Iso Fragarone-030, Iso Fragarone, 1% ETOH™, Isobutyl Furyl Propionate, Isovaleric Acid, Juniperberry Oil English Distilled SAS, Ketone Mix, Kumarone Lemon Oil 5.times-.Sas, Lemon Oil Terpeneless Sas, Lemonless Lemon Key, Lime Oil Terpeneless, Linalool 75/80% Ex Orange (Nat), Linalyl Acetate (Nat.), Mangone 5% ETOHT™, Methional, Methyl Butyric Acid (2), Methyl Ketones (Nat.), Methyl Oxycyclosulfide 719, Mushroom Extract, Natural Flavor (99% Vanillin), Nat. Cocoa Butter Distillate, Nat. Peanut Distillate, Nonan-2-One (Nat.), Nutmeg Oil East Indian, Octanal 35% (Nat,), Octen-4-one-2, Olibanum Oil English Distilled SAS, Orange Oil 15.times. Decolorized M3706, Orange Oil 950 (10.times.), Orange Oil Terpeneless 2501, Oxaromate-884, Oxycyclothione-030, Paradiff™ 0.01% ETOHGR, Paradiff™ 0.01% Grapefruit Oil, Peach Flavor Key, Peppermint Oil Redistilled Yakima, Peppermint Oil Spec. Fractions, Phenyl Ethyl 2-Methyl Butyrate, Phenyl Ethyl Acetate, Phenyl Ethyl Alcohol, Phenyl Ethyl Isovalerate, Phenyl Oxaromate-681, Pimento Berry Oil English Distilled SAS, Pimento Leaf Oil, Pimento Leaf Oil Cleaned, Pineapple Compound 15% ETOH GR, Pineapple Compound 15% PG, Popcorn Chemical, Propionic Acid, Raspberry Flavor Key, Raspberry Flavor Key, Raspberry Flavor Key, Robustone 1.0% ETOH™, Robustone™, Schinus Molle Oil, Sclareolide, Sesame Distillate Nat., Sinensals (Nat.), Spearmint Oil Terpeneless, Starter Distillate 15.times.W/S, Strawberriff, Strawberry Base, Strawberry Flavor Key, Strawberry Flavor Key, Succinic Acid, Sulfurome-015, Sweetness Modifier, Tetrahydro Terrazine-014™, Thionol-935, Thionol-966, trans-2-Hexenal, Trimenal Acetate 399 1% ETOH™, Tropical Fruit Key Base, Tropical Fruit Key Base, Undecan-2-One (Nat.), Varamol-106 10% ETOH, Varamol-106 10% NEBM5, and Varamol-106 10% PG.

Natural flavor ingredients, especially the essential oils, which benefit from the stabilizing effect of the compounds of Formula I, are obtained by well known and practiced methods. For example, they may be derived from plant materials by compression or solvent extraction. In an alternate process, odoriferous plant parts are steam distilled and the oil collected by separation from the condensed distillate. The leftover water distillate contains plant components and some volatile oils. This material is normally marketed as water. Typical flower representatives are cabbage rose (*Rosa centifolia*) flower water, matricaria water, and peppermint leaf water. A similar distillate is obtained from *Hamamelis virginiana* but is marketed primarily as a hydroalcoholic solution.

Previous mention had been made of the plant *Curcuma longa* and its use as a source of various curcumin oil pigments. These plants also serve as a source of flavor ingredients such as turmeric; the spice derived from the rhizomes of the plant. Turmeric is widely consumed in the countries of origin for a variety of uses, including use as a dietary spice, as a dietary pigment and as an Indian folk medicine for the treatment of various illnesses.

Another group of flavor ingredients which benefit from the stabilizing effect of the compounds of Formula I are the bioflavonoids and flavonoids. These compounds belong to a large series of plant-derived phenolics. In addition to their flavoring abilities, some of these compounds are deeply colored and may be used for their tinctorial attributes as well in order to impart color. Compounds belonging to this group of compounds, are, for example, Alizarin, Purpurin, Amaranth, Annatto, Anthocyanidins, Apigenin, Azulene, Betalaines and Betanines, phytolaccanin, (Blue) Gardenia, Caramel, Carotenes, Lycopene, Canthaxathin, Capsanthin/Capsorubin, Xanthophyll, Carthamin, Chlorophyll, Crocin and Crocetin, crocetin, Curcumin, desmethoxycurcumin, Indigo, Juglone, Lawsone, Luteolin, Phycocyanobilin, Pratol, Santalin, Shikonin, and alkannin.

The stabilizing compounds of Formula I are especially applicable to and beneficial with respect to sunscreen actives and sunscreen containing compositions. Sunscreen actives are ingredients that either absorb or physically block UV radiation, especially UV-B radiation, including e.g., UV-B and/or UV-A/UV-B sunblock actives. UV-B is the most damaging of ultraviolet radiation and, therefore, is the most important one to address. Also, because there are those who still desire a "natural" tan, the absence of a significant amount of UV-A sunblock active or a strongly UV-A type UV-A/UV-B sunblock active will still provide some protection against the harmful effects of UV exposure while still allowing the "tanning" waves to do their stuff. Indeed, such formulations may also contain an active ingredient that promotes tanning by amplifying the effects of UV light, e.g., melanin, L-tyrosine, tea oil, and green tea extracts. Most preferably, though, particularly since self-tanning agents such as DHA can be added to the sunscreen compositions, sunscreen compositions according to the present invention will be effective against both UV-A and UV-B radiation and have either strong UV-A/UV-B sunblock actives or the presence of an UV-A sunblock active in addition to the UV-B sunblock active.

Sunscreen actives are of two types, inorganic actives that work by reflecting the UV light and organic actives that work, predominately, by absorbing UV energy. Those that work by blocking UV light are less sensitive to photo-degradation, whereas those that work by absorbing UV energy are especially susceptible to photo-degradation. Exemplary organic sunscreen actives that will benefit from the addition of the stabilizer compounds according to Formula I above include, for example, avobenzone, butyl methoxydibenzoylmethane, cinoxate, benzophenone-8, dioxybenzone, homosalate, octylsalate, menthyl anthranilate, octocrylene, ethyhexyl methoxycinnamate, octyl methoxycinnamate, octyl salicylate, oxybenzone, padimate O, ethylhexyl salicylate, benzophenone-3, p-aminobenzoic acid (PABA), ethylhexyl dimethyl PABA, glyceryl PABA, phennylbenzimidazole sulfonic acid, sulfisobezone, trolamine salicylate, 4-methylbenzylidene camphor, bisoctrizole, bemotrizinol, ecamsule, drometrizole trisiloxane, disodium phenyl dibenzimidazole tetrasulfonate, diethylamine hydroxybenzoyl hexyl bezoate, octyl triazone, hexyl benzoate, benzophenone-4, ethyhexyl triazone, diethylhexyl butamido triazone, bisimidazylate, polysilicone-15, etc.

Although inorganic sunscreens actives, those that perform by physically blocking the UV radiation, may not benefit or may not benefit as much from the presence of the stabilizing compounds of Formula I above, the addition of the compounds of Formula I may still provide overall stabilization to the compositions as a whole. In this instance, rather than add the stabilizer additive of Formula I to the sunscreen active, it is more likely and more beneficial to add it to the formulated sunscreen composition containing the inorganic sunscreen actives. Such inorganic actives include, but are not limited to, microfine surface treated titanium dioxide and microfine untreated and surface treated zinc oxide. The titanium dioxide in the sunscreen compositions preferably has a mean primary particle size of between 5 and 150 nm, preferably between 10 and 100 nm. Titanium oxide may have an anatase, rutile, or amorphous structure. The zinc oxide in the sunscreen compositions preferably has a mean primary particle size of between 5 nm and 150 nm, preferably between 10 nm and 100 nm. Examples of suitable hydrophobically modified titanium dioxide compositions include but are not limited to the following: UV Titans® X161, M160, M262 (surface treated with stearic acid and alumina) (Kemira); Eusolex® T-2000 (surface treated with alumina and simethicone) (Merck KGaA); T-Cote® (surface treated with dimethicone) (BASF); Mirasun® TiW60 (surface treated with silica and alumina) (Rhodia); Tayaca MT100T (surface treated with aluminum stearate) (Tayaca); Tayaca MT-100SA (surface treated with silica and alumina) (Tayaca); Tayaca MT-500SA (surface treated with silica and alumina) (Tayaca); Tioveil® EUT, FIN, FLO, FPT, GCM, GPT, IPM, MOTG, OP, TG, TGOP (surface treated with silica and alumina, 40% dispersion in a range of cosmetic vehicle) (ICI); Eusolex® T-45D (surface treated with alumina and simethicone, 45% dispersion in isononoylnonaoate) (Merck KGaA); and Eusolex® T-Aqua (surface treated with aluminum hydroxide, 25% dispersion in water) (Merck KGaA). Examples of suitable untreated and hydrophobically modified zinc oxide include but are not limited to the following: Z-Cote® (uncoated microfine zinc oxide) (BASF); Z-Cote® HP-1 (surface treated with dimethicone) (BASF); Sachtotec® LA 10 (surface treated with lauric acid) (Sachtleben); Sachtotec® (uncoated microfine zinc oxide) (Sachtleben); Spectraveil® FIN, IPM, MOTG, OP, TG, TGOP (uncoated, 60% dispersion in a range of cosmetic vehicle) (101); Z-sperse® TN (untreated, dispersion in C12-15 alkyl benzoate) (Collaborative); Z-sperse® TN (untreated, dispersion in octyldodecyl neopentanoate) (Collaborative).

Most preferably, sunscreen compositions incorporating the stabilizer compounds of the present invention will comprise a combination of sunscreen actives. In this respect, it is well known that certain sunscreen actives have better stability, hence longevity, than others; while others have better absorptive capabilities, whether in reference to selectivity for UV energy of certain wavelength(s) or cumulative absorptive capabilities. Hence, by using combinations of UV sunscreen actives, one is able to provide greater overall protection. Suitable combinations are well known in the art and within the skill of a typical artisan in the field.

As noted previously, the stabilizer compounds according to Formula I may be used in a number of different applications to prevent, mitigate, or stop the degradation, particularly photodegradation, of various ingredients used in the production of a variety of products including foods, cosmetics, personal care products and household products, especially household cleaning compositions, detergents, dishwashing liquids or powders, glass or furniture cleaning and/or polishing compositions, floor cleaning and/or polishing compositions, air fresheners, etc. Such degradation may arise from inherent properties of the sensitive ingredients, such as the inherent formation of free radicals upon storage, and/or from environmental conditions such as radiation, especially visible light and, most especially, UV light; heat; oxidation, and the like, or combinations thereof. Other causes of instability may be other ingredients in the compositions containing the unstable ingredients or their degradation products. The compounds of the present invention have been found to be helpful in all these respects in preventing degradation and improving the overall stability of these ingredients individually as well as in compositions and products into which these ingredients are incorporated.

Also as noted above, the compounds of Formula I may be added directly to the ingredients, which can be in their purified or commercial form, or to concentrates and/or production premixes in which said ingredients are incorporated. Alternatively, they may be added to the final formulation or products into which the ingredients to be protected are added. As yet another alternative, they may be added in both instances, the first addition to protect the ingredients prior to use, e.g., while in storage, and the second to add further protection to the final products containing those ingredients. In either instance, they may be added by simple blending or they may be added in combination with or incorporated into a suitable carrier before combining with the ingredient or ingredient-containing blend, premix, composition, or product. Suitable carriers are those solvents, solutions, compounds and/or additives known in the art for such utility. Generally speaking, the carriers are used to dissolve or suspend the stabilizer compound of Formula I, if added as a liquid, or to aid in the dispersion of the stabilizer compound, if added as a solid, to enhance its incorporation into the ingredient, the ingredient concentrate, or the products or intermediates and/or premixes containing the ingredients without adversely affecting the end use of the finished products into which they are incorporated.

The present invention also pertains to food, cosmetic, personal care and household products containing one or more ingredients such as, but not limited to, antioxidants, flavors, fragrances, sunscreens, colorants, dyes, thickeners, and the like, that manifest instability due to inherent degradation and/or environmental factors such as visible and/or UV light, heat, and the like, and which also contain a stabilizingly effective amount of a compound according to Formula I above. These compounds provide enhanced stability, particularly photostability, to a variety of unstable and/or photosensitive compounds, especially those based on or having poly-unsaturation and/or aromatic groups or moieties, as compared to the same compounds in the absence of a stabilizer, particularly a stabilizer compound of Formula I. Furthermore, as demonstrated in the Examples below, the stabilizer compounds of Formula I oftentimes provide even enhanced stability as compared to similar compositions employing conventional stabilizers. Though difficult to assign a specific degree of enhanced stability of the materials into which they are incorporated, especially in light of the myriad of factors and variables that influence stability, it is generally appreciated that the compounds of Formula I increase shelf life of the materials into which they are incorporated; prevent, mitigate or delay the onset of the loss of the properties of the materials into which they are incorporated; enable the use of such materials and/or packaging and application options that are not otherwise suitable in light of the instability of the materials or one or more components thereof. In general terms, while even an enhancement in stability of 10% or more, or preferably 25% or more, as a result of the use of the compounds of Formula I is beneficial, these compounds oftentimes result in enhanced stability of 40% or more, even 50% or more as reflected in or manifested by longer shelf stability, color retention, activity retention, reduced loss of actives, and the like as compared to the same material without the compound of Formula 1.

The use of the compounds according to Formula I is especially beneficial in cosmetic and personal care products, most especially those intended for topical skin application. Thus, they not only stabilize the ingredients in the cosmetic or personal care composition, thereby prolonging their efficacy for their intended application, but also provide beneficial therapy to the skin to which they are applied. Indeed, it is also contemplated that the compounds according to Formula I may be suitable as active ingredients in their own right, with or without other active ingredients, whether photosensitive or not.

As noted already, cosmetic and personal care compositions intended for application to the skin typically include a plurality of active ingredients, many of which manifest stability, namely instability, issues, as discussed at length above. Additionally, these cosmetic and personal care compositions further comprise at least one and most often a plurality of "inert" or "inactive" components which affect the nature and/or physical attributes of the composition or product including its state of being, its viscosity, physical stability, ease and nature of application, and the like. These inert or inactive components, and preferably the active ingredients themselves, are generally described as being "dermatologically-acceptable" meaning that they are generally suitable for use in compositions intended for human skin contact without concern for undue toxicity, incompatibility, instability, allergic response, and the like. These active ingredients and inert or inactive components include, but are not limited to, carriers, emollients, humectants, anti-inflammatory agents, self-tanning agents, and the like. Oftentimes, these cosmetic and skin care products include optional adjunct ingredients including, but not limited to, preservatives, waterproofing agents, anti-foam agents, plant extracts (Aloe vera, witch hazel, cucumber, etc); opacifiers, stabilizers; skin conditioning agents; and the like, each in amounts effective to accomplish their respective functions. Again, this is in addition to the primary actives mentioned above. Such compositions and products are well known; though the use therein of the stabilizing compounds according to Formula I are not. Exemplary compositions which can be modified in accordance with the present teachings include those described in US 2008/0286217 A1 and US 2009/0137534A1 (Chaudhuri et al.), which are hereby incorporated herein by reference in their entirety.

Generally speaking, any known carrier or base composition employed in traditional cosmetic and skin care, including sunscreen, compositions may be used in the practice of the present invention. Suitable carriers and carrier compositions are described at length in, for example, Gonzalez et. al.—U.S. Pat. No. 7,186,404; Aust et. al.—U.S. Pat. No. 7,175,834; Roseaver et. al.—U.S. Pat. No. 7,172,754; Simoulidis et. al.—U.S. Pat. No. 7,175,835; Mongiat et. al.—U.S. Pat. No. 7,101,536; Maniscalco—U.S. Pat. No. 7,078,022; Forestier et. al. U.S. Pat. No. 5,175,340, 5,567,418, 5,538,716, and 5,951,968; Defiandre et, al.—U.S. Pat. No. 5,670,140; Chaudhuri—U.S. Pat. No. 6,831,191, 6,602,515, 7,166,273, 6,936,735, and 6,699,463; Chaudhuri et, al.—U.S. Pat. No. 6,165,450 and 7,150,876; Banda et. al, U.S. Pat. No. 6,962,692; and Wang et. al. U.S. Pat. No. 5,830,441, all of which are incorporated herein by reference in their entirety. Those skilled in the art will readily recognize and appreciate what carriers may be employed in light of the intended form and/or delivery method for the novel cosmetic and skin care compositions of the present teachings.

Suitable emollients include those agents known for softening the skin which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Oily ester emollients include those selected from the following: triglyceride esters, acetoglyceride esters, ethoxylated glycerides, alkyl esters of fatty acids, ether esters, polyhydric alcohol esters, wax esters and combinations of the foregoing. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylic/capric triglycerides, propylene glycol dicaprylate/dicaprate and decyl oleate.

Suitable humectants include various polyhydric alcohols, especially polyalkylene glycols and, more preferably, alkylene polyols and their derivatives. Exemplary humectants include propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2,6-hexanetriol, glycerin, ethoxylated glycerin, propoxylated glycerin, compatible solutes, such as ectoin, hydroxectoin, taurines, carnithine, acetyl carnithine and mixtures thereof. When employed in effective amounts, generally from 1 to 30%, preferably from 2 to 20%, by weight of the cosmetic or skin care compositions, especially sunscreen composition, into which they are incorporated, these additives serve as skin moisturizers as well as reduce scaling and stimulate the removal of built-up scale from the skin.

Examples of anti-inflammatory ingredients include, but are not limited to, bisabolol, curcurmin and its derivatives, retinoids, meroterpenes (especially bakuchiol and corylifolin), flavonoids and other polyphenolics etc. These and other anti-inflammatory agents, as well as additional anti-oxidants and the like, are disclosed in Gupta et. al.—US 2005/0048008A1.

Examples of self-tanning ingredients include, but are not limited to, dihydroxyacetone and erythrulose.

The cosmetic and skin care compositions of the present invention may also include one or more skin penetrants. These are additives that, when applied to the skin, have a direct effect on the permeability of the skin barrier: increasing the speed with which and/or the amount by which certain other compounds are able to penetrate into the skin layers. Exemplary organic penetration enhancers include dimethyl sulfoxide; isopropyl myristate; decyl, undecyl or dodecyl alcohol; propylene glycol; polyethylene glycol; azone; $C_{9-11}$, $C_{12-13}$ or $C_{12-15}$ fatty alcohols; alkyl pyrrolidones; lecithin; etc. Surfactants can also be used as penetration enhancers.

As noted above, because of the antioxidant properties of the compounds according to Formula above, these compounds as especially useful in cosmetic and skin care compositions, most especially sunscreen compositions and other products that also serve as sunscreen compositions or have sunscreen capabilities, i.e., compositions that are effective in reducing or preventing skin damage due to UV exposure, especially exposure to the sun. As such, the present invention also pertains to a method of protecting skin from damage due to UV exposure said method comprising the step of applying of the aforementioned cosmetic and skin care compositions containing the stabilizer compounds of Formula I. Obviously those compositions according to the present invention which are specifically formulated as sunscreen compositions are applied to those areas of the skin that are or are likely to be exposed to sun light; however, these compositions may also be applied to areas of the skin that are not typically exposed to the sun but that nevertheless have exposure to the penetrating UV rays. For example, tee shirts and other light fabrics offer minimal protection against sun exposure, especially to UV rays. Thus, conceivably, the inventive sunscreen compositions may be applied to essentially all areas of the body, including those typically covered by clothing.

The amount of the cosmetic or skin care composition that is applied to the skin surface depends in large part upon the composition and its intended purpose. For example, typical cosmetics are applied to give the desired skin appearance and coloration, whether as a base composition or a top coat composition. The amount also depends upon the form of the composition to be applied and its mode of application. For example, a spray formulation may be applied so as to provide a light, even coat on the skin. Lotions, creams, gels and the like are, as already noted typically applied to provide the desired appearance or, in the case of true sunscreen products, to provide an even coat over the area treated. In the case of sunscreen compositions, the amount applied is typically from about 1 to 2 ounces for the entire body, i.e., for the exposed skin of an "average individual" wearing a swimsuit and standing 5 feet 4 inches tall, weighing 150 pounds, and having a 32 inch waist. This translates to an application rate of about 2 $mg/cm^2$ of skin. On the face, a typical application rate is ¼ to ⅓ of a teaspoon. Generally speaking, the application rate will be from about 0.1 to about 10 $mg/cm^2$, preferably from about 1 to about 3 $mg/cm^2$, of skin.

In addition to the above-mentioned photo-protective benefits of the cosmetic and skin care compositions according to the present teachings, the continual, preferably daily, use these cosmetic and skin care products, regardless of whether one anticipates UV exposure or not, provides a number of benefits to one's skin, again owing to the antioxidant activity of the stabilizer compounds according to Formula I. For example, the continual/daily use of these compositions will delay the appearance or manifestation of fine lines, enhance extracellular matrix cohesion, reduce the appearance of spider veins, improving skin firmness and elasticity: skin effects that are not only a result of exposure to the sun but also the natural aging process. In this regard, it is to be further noted that the stabilizing compounds of Formula I are found to modulate the expression of certain genes and proteins associated with skin health and appearance and with reversing some of the signs of aging manifested in the skin.

The compositions according to the present invention may take any form consistent with for the type of product formulated, its intended purpose, and method of application. Typically, these compositions, especially those for cosmetic and personal care applications are in the form of creams, ointments, suspensions, powders, oils, lotions, oleo alcoholic lotions, fatty gels, oleo-alcoholic gels and lotions, solid sticks, foams, emulsions, liquid dispersions, sprays and aerosols. More specific forms include: lotions, lipsticks, foundations, makeup, loose or press powder, eye blush, eye shadow, shampoo, conditioner and nail lacquer. The household formulations can be in the form of solids sticks, solutions, sprays, aerosols, foams, liquid dispersions, loose powders and the like.

Although the foregoing discussion has been primarily made with respect to cosmetic, personal care and, to a lesser extent, food products and ingredients, it is to be understood that the teachings of the present invention are applicable in general to any number of compositions and products, whether intended for industrial, pharmaceutical and/or consumer use or application, including cleaners, sanitizers, odor controlling agents, etc., having components that are subject to degradation and/or oxidation, particularly that arising from or induced by light exposure, most especially UV radiation. For example, in addition to those ingredients mentioned above, many pharmaceutical actives/pharmacological ingredients as well as the compositions and products into which they are incorporated have a high degree of instability to long term storage and/or light, especially UV light, exposure. Such compounds and ingredients will also benefit from the addition of the stabilizer compounds of Formula I.

Generally speaking, as discussed at length above, the compounds according to Formula I above have been found to prevent the degradation of a number of unstable, including photosensitive, ingredients and compounds as well as compositions into which they are incorporated. This effect is particularly noted where the ingredients or compositions containing those ingredients are exposed to conditions under which the instability manifests itself and/or is accelerated or enhanced, especially upon exposure to light and/or heat, most especially UV light. Additionally, as noted, it has been found that the additive compounds according to the present teaching also provide extended shelf life and, hence, storage stability, to those ingredients and the compositions containing the same that suffer from degradation and/or loss of efficacy, even in the absence of the otherwise degrading conditions.

Having described the invention in general terms and by was of an overall discussion, the following examples provide further support and evidence the benefits and applications of the present invention.

EXAMPLES

Example 1

Synthesis of
3-(3,4,5-trimethoxybenzylidene)-2,4-pentanedione 3-(3,4,5-trimethoxybenzylidene)-2,4-pentanedione (hereinafter "HSS") was prepared by the condensation of 3,4,5-trimethoxy benzaldehyde with acetyl acetone in the presence of piperidine and cyclohexane as the reaction medium at reflux temperature under continuous azeotropic water removal. The reaction takes about eight hours to complete. The reaction product was purified by crystallization with methanol. The typical yield of HSS is about 68% with a purity, as determined by GC, of 99.1%. HSS is an off-white free-flowing powder with a melting point of 83-86° C. with a $\lambda_{max}$ at 319 nm.

Example 2

Synthesis of
3-(3,4-dimethoxybenzylidene)-2,4-pentanedione 3-(3,4-dimethoxybenzylidene)-2,4-pentanedione (hereinafter "Compound 2") was prepared by the condensation of 3,4-dimethoxy benzaldehyde with acetyl acetone in the presence of piperidine and cyclohexane as the reaction medium at reflux temperature under continuous azeotropic water removal. The reaction takes about eight hours to complete. The reaction product was purified by crystallization with methanol. The typical yield of Compound 2 is about 67% with a purity, as determined by GC, of about 99.5%. Compound 2 is an off-white free-flowing powder having a melting point of 104-108° C. with a $\lambda_{max}$ at 335 nm.

Example 3

Synthesis of
3-(4-methoxybenzylidene)-2,4-pentanedione 3-(4-methoxybenzylidene)-2,4-pentanedione was prepared by the condensation of 4-methoxy benzaldehyde with acetyl acetone in the presence of piperidine and cyclohexane as the reaction medium at reflux temperature under continuous azeotropic water removal. The reaction takes about eight hours to complete. The reaction product was purified by crystallization with methanol and yields about 70% 3-(4-methoxybenzylidene)-2,4-pentanedione (hereinafter "Compound 3") with a purity, as determined by GC, of about 99.6%. Compound 3 is an off-white free-flowing powder having a melting point of 82-84° C. with a $\lambda_{max}$ at 319 nm.

Example 4

Hydrolytic stability of
3-(3,4,5-Trimethoxybenzylidene)-2,4-pentanedione

A series of hydrolytic stability tests were conducted on the compound of Example 1, HSS, as follows pH7: 2.5 g of samples of HSS were placed in 100 ml round bottom flasks and 50 ml of double distilled water (pH 7) added to each. One set of samples was kept at 40° and the other at 60° C. and for 4 hrs and 8 hrs. Thereafter each sample was filtered and the solids dried.

pH 8: 2.5 g of samples of HSS were placed in 100 ml round bottom flasks and 50 ml of double distilled water which had been adjusted to pH 8 using 0.01N NaOH solution added to each. One set of samples was kept at 40° and the other at 60° C. for 4 hrs and 8 hrs. Thereafter each sample was filtered and the solids dried.

pH 9: 2.5 g of samples of HSS were placed in 100 ml round bottom flasks and 50 ml of double distilled water which had been adjusted to pH 9 using 0.1N NaOH solution added to each. One set of samples was kept at 40° and the other at 60° C. for 4 hrs and 8 hrs. Thereafter each sample was filtered and the solids dried.

Each dried sample was analyzed by gas chromatography using an HP-5, 15 m, 0.53 mm id, capillary column with following set-up and test parameters:
  Injection temperature: 250° C.
  Oven temp: 50° C. (2 min), 10° C. to 260° C. (20 min)
  Detector: FID
  Detector temp: 260° C.
  Carrier gas: Nitrogen
  Column flow: 3.0 ml/min
  Split ratio: 5:1
  Injection Volume: 1 micro liter
  Sample concentration: 100 mg/ml in Methanol The results of the analysis of each sample were as presented in Table 4. The initial purity of the HSS used to make Samples A through F was 98.9% as determined by the aforementioned GC procedure. As indicated in Table 4, HSS was found to be stable at pH 7, 8, and 9 at 40° C. and at 60° C. for at least for 8 hrs.

TABLE 4

| | GC purity (Area %) | | | | | |
|---|---|---|---|---|---|---|
| | At RT (~27° C.) | | At 40° C. | | At 60° C. | |
| | 4 h | 8 h | 4 h | 8 h | 4 h | 8 h |
| pH 7 | 98.8 | 99.0 | 98.9 | 99.1 | 98.6 | 99.0 |
| pH 8 | 98.7 | 99.2 | 98.9 | 99.1 | 99.2 | 99.0 |
| pH 9 | 98.8 | 98.8 | 99.0 | 98.9 | 99.1 | 98.8 |

Example 5

Stability of
3-(3,4,5-trimethoxybenzylidene)-pentane-2,4-dione
in the Presence of Iron and Copper A base buffer solution was prepared by dissolving 13.608 g of sodium acetate in 1000 ml water and then adjusting the pH to 6.5 with acetic acid to form a 0.1 M acetate solution and then combining 75 parts by weight of this solution with 25 parts by weight ethanol.

A copper sulfate solution was prepared by dissolving 24.968 mg of copper sulfate ($CuSO_4.5H_2O$) in 100 ml of the base buffer solution.

A ferric sulfate solution was prepared by dissolving 16.22 mg of copper sulfate in 100 ml of the base buffer solution.

Finally a 100 μM test solution of HSS was prepared by dissolving 27.8 mg of HSS in 10 ml of the base buffer solution and then diluting 0.1 ml of this solution to 10 ml with additional base buffer solution.

Two test solutions were prepared as follows:

Copper Stability: 0.1 ml of the 100 μM solution of HSS was combined with 0.1 ml of the 10 μM $CuSO_4$ solution in a 10 ml volumetric flask and additional base buffer solution added to make up to volume (to 10 ml).

Iron Stability: 0.1 ml of the 100 μM solution of HSS was combined with 0.1 ml of the 10 μM $FeSO_4$ solution in a 10 ml volumetric flask and additional base buffer solution added to make up to volume (to 10 ml).

The two test solutions and a sample of the HSS solution were then evaluated to assess what, if any, auto-oxidation of the HSS occurred in the presence of $Cu^{2+}$ and $Fe^{3+}$ ions. Stability or instability was evaluated by monitoring the absorbance at 319 nm for HSS at room temperature using a Shimadzu spectrophotometer. Based on the observations, no change was seen in the $\lambda_{max}$ and extinction coefficient and the overall pattern of UV spectrum of the HSS remained same. Accordingly, it was concluded that HSS was stable irrespective of the presence of iron and copper ions.

Example 6

Photostability Studies

A comparative photostabilization study was conducted comparing the photostabilization efficacy of the compound of Example 1, HSS, and the compound of Example 3 (Compound 3) with Octocrylene and Oxynex® ST in the stabilization of avobenzone. Samples for evaluation were prepared as follows:

Solutions in ethanol are prepared at respective concentrations of photosensitive materials and photostabilizer (typically 1:1 to 1:5 weight ratio). A base test solution of 3% Avobenzone+5% Octyl salicylate +10% Homoslate in Ethanol (the "Test Solution") was made. Seven additional solutions were prepared by adding 2% Synoxyl™ HSS, 4% Synoxyl™ HSS, 4% Compound 3, 2% Octocrylene, 4% Octocrylene, 2% Oxynex® ST, and 2% dehydrozingerone methyl ether, respectively, to seven aliquots of the Test Solution.

Samples of each solution were prepared as ultrathin films between two quartz plates so as to obtain a minimum of 90% light transmission over the entire spectrum range of non absorbing chromophores. For example, ingredients which absorb only in the UV range were tested in formulation to obtain a minimum of 90% light transmission over the visible range. Each sample was then irradiated under sun simulator (754 W/m², 2 MED/h, UV dose from 20 to 100 Joules/cm²) for various durations and light absorption spectra recorded for each sample at given times. The maximal absorption band λmax of each solution was determined before and after irradiation. The amount of the photosensitive materials remaining in solution after irradiation was calculated as the ratio of their two maximal absorptions. The tests conducted and the results obtained therewith are presented in Table 5.

TABLE 5

| | UV dose in Joules/cm² | | | | | |
|---|---|---|---|---|---|---|
| | 0 | 20 | 40 | 60 | 80 | 100 |
| Product | % remaining | | | | | |
| Test Solution | 100% | 36% | 28% | 23% | 20% | 18% |
| 4% Synoxyl ™ HSS | 100% | 96% | 90% | 84% | 80% | 76% |
| 2% Synoxyl ™ HSS | 100% | 96% | 90% | 84% | 77% | 70% |
| 4% Compound 3 | 100% | 96% | 90% | 80% | 73% | 68% |
| 4% Octocrylene | 100% | 94% | 83% | 73% | 67% | 60% |
| 2% Octocrylene | 100% | 92% | 80% | 68% | 64% | 58% |
| 2% Oxynex ® ST | 100% | 90% | 80% | 58% | 42% | 31% |
| 2% Dehydrozingerone methyl ether | 100% | 59% | 26% | Not done | Not done | Not done |

As seen from the results shown in Table 5, the inventive stabilizer of the present invention performed markedly better than either of the commercially available products at all levels of exposure.

Example 7

Sunscreen Formulation

A base sunscreen composition having the formulation set forth in Table 6 was prepared. Three samples of this were taken for photostability testing according to the method of Example 6 above. The first sample, the Control, was not modified whereas the two remaining samples were modified by incorporating therein 2% of the compound of Example 1, HSS, and 4% octocrylene, respectively. The three formulations were prepared by first preparing each of Phase A1 and A2 and then dispersing Phase A2 in Phase A1 with agitation and heating to 75 C. Phase B was prepared and heated to 75° C. Phase B is then combined with the Phase A mixture with continuous stirring. The combination was subsequently homogenized for 2-3 minutes, and the batch cooled to 45° C. Phases C and were separately prepared and then mixed with the cooled batch until uniform.

As with Example 6, each was exposed to irradiation for various durations and the photostability tested. The results for these evaluations were as presented in Table 7. As evidenced from the results shown in Table 7, the stabilizer compound of the present invention performed markedly better than that of the conventional photostabilizer in the formulated product.

This result translates to longer shelf stability of the product as well as, and perhaps more importantly, a longer efficacy when applied to the skin.

Example 8

Broad Spectrum Sunscreen Formulation

A second broad spectrum sunscreen composition, estimated SPF 35, is made according to the formulation set forth in Table 8. The composition is prepared by dispersing Phase A2 in Phase A1 with agitation and heating to 75° C. Phase B is then prepared and heated to 75° C. before being added to the Phase A mixture with continuous stirring. The mixture is then homogenized for 2-3 minutes and, subsequently cooled to 45° C. Thereafter, Phases C and D are prepared and sequentially added to the cooled mixture until uniform.

tion in order to evaluate its ability to reduce the amount of dye fading following exposure to fluorescent lighting. The sample was prepared by dissolving 0.4 g of HSS in 5 ml of ethanol and then adding the solution to 120 g of Suave® Natural Fresh Mountain Strawberry Shampoo with agitation and agitated for 15 minutes. A sample of the unmodified shampoo and the modified shampoo are then placed into 20 ml glass scintillation vials. Both sets of vials were weathered under fluorescent light aging at ambient temperature for 4 weeks. The L*a*b coordinates before and after exposure are measured using X-Rite 938 Spectro-densitometer. Color change is expressed as Delta E (ΔE) which is calculated by the formula:

$$\Delta E = [(\Delta L^*)^2 + (\Delta a^*)^2 + (\Delta b^*)^2]^{1/2}$$

TABLE 6

| | | Test Sample | | |
|---|---|---|---|---|
| | | 1 | 2 | 3 |
| INCI Name | Trade Name/Manufacturer | % w/w | % w/w | % w/w |
| Phase A-1 | | | | |
| Deionized water | | qs | qs | qs |
| Disodium EDTA | Titriplex III/Merck | 0.05 | 0.05 | 0.05 |
| Phase A-2 | | | | |
| Acrylates/C10-30 Alkyl Acrylate Crosspolymer | Carbopol Ultrez 21/Goodrich | 0.20 | 0.20 | 0.20 |
| Xanthan Gum | Vanzan NF/Vanderbilt | 0.15 | 0.15 | 0.15 |
| Phase B | | | | |
| Dimethicone | DC200fluid, 100 cst/Dow Corning | 1.50 | 1.50 | 1.50 |
| Cetyl alcohol, glyceryl stearate, PEG-75, ceteth-20 and teareth-20 | Emolium Delta/Gattefosse | 4.00 | 4.00 | 4.00 |
| C30-38 Olefin/Isopropyl Maleate/MA Copolymer | Performa V1608/New Phase Technologies | 1.00 | 1.00 | 1.00 |
| Dibutyl Adipate | Cetiol B/Cognis | 6.00 | 6.00 | 6.00 |
| C12-15 Alkyl Benzoate | Finsolv TN/Fintex | 6.00 | 6.00 | 6.00 |
| Butyl methoxydibenzoylmethane | Eusolex 9020/EMD Chemicals | 2.00 | 2.00 | 2.00 |
| Phase C | | | | |
| 3-(3,4,5-trimethoxybenzylidene)-2,4-pentanedione | Synoxy ™ HSS/Sytheon Ltd. | — | 2.00 | — |
| Octocrylene | Eusolex OCR/EMD Chemicals | — | — | 4.00 |
| Ethoxydiglycol | Transcutol CG/Gattefosse | 5.00 | 5.00 | 5.00 |
| Phase D | | | | |
| Aminomethylpropanol | AMP-95 | 0.15 | 0.15 | 0.15 |
| Phenoxyethanol (and) Isopropylparaben (and) Methylparaben (and) Butylparaben | Phenonip/Clariant | 1.00 | 1.00 | 1.00 |
| Total | | 100 | 100 | 100 |

TABLE 7

| | UV dose in Joules/cm² | | | |
|---|---|---|---|---|
| Test Sample | 0 | 20 | 40 | 60 |
| 1—Control | 100% | 60% | 31% | 21% |
| 2—2% Synoxyl ™ HSS | 100% | 96% | 92% | 88% |
| 3—4% Octocrylene | 100% | 94% | 89% | 82% |

Example 9

Stabilization of Colored Shampoo

The stabilizer compound according to Example 1, Synoxyl™ HSS, was added to a commercial shampoo formula-

TABLE 8

| INCI Name | Trade Name/Manufacturer | % w/w |
|---|---|---|
| Phase A-1 | | |
| Deionized water | | 59.05 |
| Disodium EDTA | Titriplex III/Merck | 0.05 |
| Propylene Glycol | Propylene Glycol/Lyondell | 3.00 |
| Glycerin | Emery 916/Cognis | 2.00 |
| Phase A-2 | | |
| Acrylates/C10-30 Alkyl Acrylate Crosspolymer | Carbopol Ultrez 21/Goodrich | 0.10 |
| Xanthan Gum | Vanzan NF/Vanderbilt | 0.10 |
| Phase B | | |
| Dimethicone | DC200fluid, 100 cst/Dow Corning | 0.50 |

TABLE 8-continued

| INCI Name | Trade Name/Manufacturer | % w/w |
|---|---|---|
| Cetyl alcohol, glyceryl stearate, PEG-75, Ceteth-20 and teareth-20 | Emolium Delta/Gattefosse | 3.00 |
| C30-38 Olefin/Isopropyl Maleate/MA Copolymer | Performa V1608/New Phase Technologies | 1.00 |
| Dibutyl Adipate | Cetiol B/Cognis | 4.00 |
| C12-15 Alkyl Benzoate | Finsolv TN/Fintex | 2.00 |
| Butyl methoxydibenzoylmethane | Eusolex ® 9020/EMD Chemicals | 2.00 |
| 3-(3,4,5-trimethoxybenzylidene)-2,4-pentanedione | Synoxyl ™ HSS/Sytheon Ltd. | 2.00 |
| Homosalate | Eusolex ® HMS/EMD Chemicals | 15.00 |
| Octisalate | Eusolex ® OS/EMD Chemicals | 5.00 |
| Phase C | | |
| Triethanolamine (99%) | TEA 99%/Union Carbide | 0.20 |
| Phase D | | |
| Phenoxyethanol (and) Isopropylparaben (and) Methylparaben (and) Butylparaben | Phenonip/Clariant | 1.00 |
| Total | | 100.00 |

Following the 4 week exposure the change in color, Delta E, was 21.6 for the unmodified shampoo and 12.3 for the modified shampoo. This demonstrates the marked efficacy of the compounds of the present invention in prevention color change, i.e., improved color fastness, in compositions having photosensitive colorants.

Example 10

Photostabilization of Water-Soluble Dyes

The stabilizer compound Synoxyl™ HSS according to Example 1 was added to the two dye compositions of Table 9, one containing Yellow No 5 and the other Red No 40, in order to evaluate its ability to reduce the extent of color fading resulting from their exposure to solar simulated light. In both formulations without the Synoxyl™ HSS, visible and marked color fading was noted following just 2 hours of light exposure. On the other hand, those formulations with the Synoxyl™ HSS failed to manifest color fading even after exposure to light for ~40 hours.

TABLE 9

| INC Name | Concentration |
|---|---|
| Sodium Laureth Ether Sulfate | 11% |
| Cocamidopropyl Betaine | 3.5% |
| PEG-20 Glyceryl Laurate | 1% |
| FD&C Yellow No 5 (CI 19140) or FD&C Red No 40 (CI 16035) | 0.001% |
| Synoxyl ™ HSS | 0.05%/no stabilizer |
| Water added to | 100 ml |

Without further elaboration, it is believed that one skilled in the art can, using the preceding description, can utilize the present invention to its fullest extent. Furthermore, while the present invention has been described with respect to aforementioned specific embodiments and examples, it should be appreciated that other embodiments utilizing the concept of the present invention are possible, and within the skill of one in the art, without departing from the scope of the invention.

The preceding preferred specific embodiments are, therefore, to be construed as merely illustrative, and not limitative of the remainder of the disclosure in any way whatsoever. Finally, for avoidance of doubt, it is to be understood that all publications and patents references, including published patent applications, referenced herein are hereby incorporated herein in their entirety.

I claim:

1. A method of enhancing the stabiiity, mitigating the degradation, or both of photo- and/or thermal- sensitive ingredients of food, cosmetic, personal care, pharmaceutical/medicinal, household or agrichemical products, said method comprising combining an effective amount of one or more 2,4-pentanedione compounds with the ingredient(s) to be protected, wherein the 2,4-pentanedione compounds are of the Formula I:

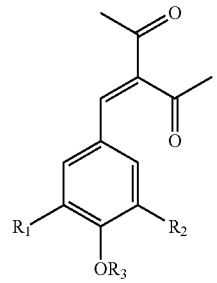

wherein $R_1$ and $R_2$, which may be the same or different, are independently alkoxy, wherein the alkoxy groups are linear or branched and have from 1 to 8 carbon atoms, and wherein $R_3$ is methyl.

2. The method of claim 1 wherein the alkoxy groups $R_1$ and $R_2$ have from 1 to 6 carbon atoms.

3. The method of claim 1 wherein the alkoxy groups $R_1$ and $R_2$ have from 1 to 4 carbon atoms.

4. The method of claim 1 wherein $R_3$ is methyl and $R_1=R_2=OCH_3$.

5. The method of claim 1 wherein the 2,4-pentanedione compound is combined with one or more ingredients to be protected by the compound in an amount of from about 0.001 to about 15 weight percent based on the weight of said one or more ingredients.

6. The method of claim 1 wherein the household product is a household cleaning, washing detergent, sanitation or odor control product.

7. The method of claim 1 wherein the 2,4-pentanedione compound is combined with the ingredients to be protected in an amount of from about 0.01 to about 15 weight percent based on the total weight of the product.

8. The method of claim 1 wherein a plurality of compounds according to Formula I, a combination of at least one compound according to Formula I and an antioxidant, a combination of at least one compound according to Formula I and a stabilizer, or a combination of at least one compound according to Formula I and a combination of an antioxidant and a stabilizer are employed.

9. The method of claim 1 wherein the compound of formula 1 is used in combination with a singlet oxygen quencher.

10. The method of claim 1 wherein the 2,4-pentanedione compound is combined with one or more ingredients to be protected by the compound in an amount of from about 0.5 to about 5 weight percent based on the weight of said one or more ingredients.

11. The method of claim 1 wherein the 2,4-pentanedione compound is combined with the ingredients to be protected in an amount of from about 0.1 to about 10 weight percent based on the total weight of the product.

12. The method of claim 1 wherein the 2,4-pentanedione compound is combined with the ingredients to be protected in an amount of from about 0.5 to about 5 weight percent based on the total weight of the product.

13. The method of claim 1 wherein a plurality of compounds of formula 1 are used.

14. The method of claim 1 wherein the product is a cosmetic, personal care, or pharmaceutical/medicinal product.

* * * * *